(12) United States Patent
Bennett et al.

(10) Patent No.: US 8,887,090 B2
(45) Date of Patent: Nov. 11, 2014

(54) SURFACING OF DETAILED INFORMATION VIA FORMLETS

(71) Applicant: General Electric Company, Schenectady, NY (US)

(72) Inventors: Benjamin Bennett, Murray, UT (US); John Brimm, Murray, UT (US); David Cronin, San Ramon, CA (US)

(73) Assignees: General Electric Company, Schenectady, NY (US); IHC Health Services, Inc., Salt Lake City, UT (US)

( * ) Notice: Subject to any disclaimer, the term of this patent is extended or adjusted under 35 U.S.C. 154(b) by 0 days.

(21) Appl. No.: 13/665,823

(22) Filed: Oct. 31, 2012

(65) Prior Publication Data

US 2014/0123061 A1     May 1, 2014

(51) Int. Cl.
     *G06F 3/048*        (2013.01)
     *G06F 19/00*       (2011.01)

(52) U.S. Cl.
     CPC ....................................... *G06F 19/30* (2013.01)
     USPC ......................................................... 715/808

(58) Field of Classification Search
None
See application file for complete search history.

(56) References Cited

U.S. PATENT DOCUMENTS

| | | | | |
|---|---|---|---|---|
| 5,077,666 | A * | 12/1991 | Brimm et al. | 705/2 |
| 2006/0174210 | A1* | 8/2006 | Richards et al. | 715/769 |
| 2007/0033535 | A1* | 2/2007 | Cornacchia, III | 715/762 |
| 2007/0094597 | A1* | 4/2007 | Rostom | 715/700 |
| 2008/0082357 | A1* | 4/2008 | Schmitt et al. | 705/2 |
| 2010/0305965 | A1* | 12/2010 | Benjamin et al. | 705/2 |
| 2011/0040572 | A1* | 2/2011 | Chmiel et al. | 705/2 |
| 2012/0215562 | A1* | 8/2012 | James et al. | 705/3 |
| 2012/0239415 | A1* | 9/2012 | Agrawal et al. | 705/2 |
| 2012/0246105 | A1* | 9/2012 | James | 706/47 |
| 2013/0173602 | A1* | 7/2013 | James et al. | 707/722 |

* cited by examiner

*Primary Examiner* — Matt Kim
*Assistant Examiner* — Maryam Ipakchi
(74) *Attorney, Agent, or Firm* — Hanley, Flight and Zimmerman, LLC

(57) ABSTRACT

Certain examples provide systems, methods, apparatus, etc., to provide varying levels of detail in clinical data for one or more patients to a user. An example method to surface varying degrees of patient data via a formlet-based user interface includes providing a high-level view of data for one or more patients, the high-level view having a first level of detail. The example method includes generating, in response to a hover over a portion of the high-level view, a hover view providing a second level of detail of the data associated with the portion of the high-level view. The example method includes providing an inspector to access a third level of detail of the data. The example method includes generating a fourth level of detail in response to a trigger within the inspector.

20 Claims, 30 Drawing Sheets

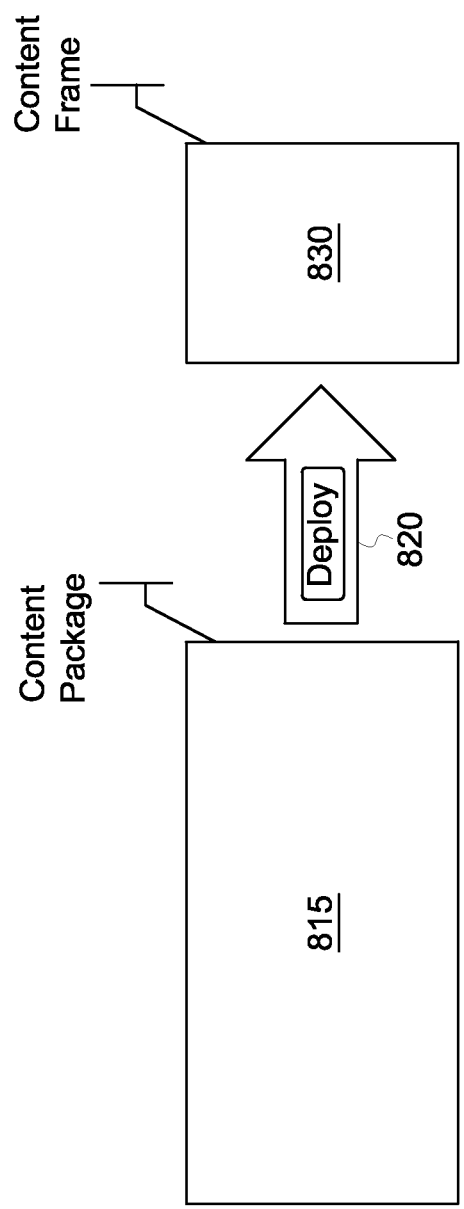

SURFACING OF DETAILED INFORMATION VIA FORMLETS

FIELD

The present invention generally relates to healthcare information systems and, more particularly, to methods and apparatus for content-driven systems and methods.

BACKGROUND

Healthcare environments, such as hospitals and clinics, typically include information systems (e.g., electronic medical record (EMR) systems, lab information systems, outpatient and inpatient systems, hospital information systems (HIS), radiology information systems (RIS), storage systems, picture archiving and communication systems (PACS), etc.) to manage clinical information such as, for example, patient medical histories, imaging data, test results, diagnosis information, management information, financial information, and/or scheduling information. These healthcare information systems are used to implement different types of workflows in which clinical information is generated, updated, augmented, and/or otherwise processed for one or more purposes.

BRIEF DESCRIPTION

Certain examples provide systems, methods, apparatus, etc., to provide varying levels of detail in clinical data for one or more patients to a user.

Certain examples provide a method to surface varying degrees of patient data via a formlet-based user interface. The example method includes providing a high-level view of data for one or more patients, the high-level view having a first level of detail. The example method includes generating, in response to a hover over a portion of the high-level view, a hover view providing a second level of detail of the data associated with the portion of the high-level view. The example method includes providing an inspector to access a third level of detail of the data. The example method includes generating a fourth level of detail in response to a trigger within the inspector.

Certain examples provide a computer readable storage medium including computer program code to be executed by a processor, the computer program code, when executed, to implement a method to surface varying degrees of patient data via a formlet-based user interface. The example method includes providing a high-level view of data for one or more patients, the high-level view having a first level of detail. The example method includes generating, in response to a hover over a portion of the high-level view, a hover view providing a second level of detail of the data associated with the portion of the high-level view. The example method includes providing an inspector to access a third level of detail of the data. The example method includes generating a fourth level of detail in response to a trigger within the inspector.

Certain examples provide a system including an interface to provide a high-level view of data for one or more patients, the high-level view having a first level of detail. The example system includes a hover view to a second level of detail of the data associated with the portion of the high-level view in response to a hover over a portion of the high-level view. The example system includes an inspector to provide access to a third level of detail of the data, wherein the inspector is to provide a fourth level of detail of the data in response to a trigger within the inspector.

BRIEF DESCRIPTION OF SEVERAL VIEWS OF THE DRAWINGS

FIGS. 20-26 illustrate a plurality of example views of patient data formed from and configurable via a plurality of formlets

Figure 1:
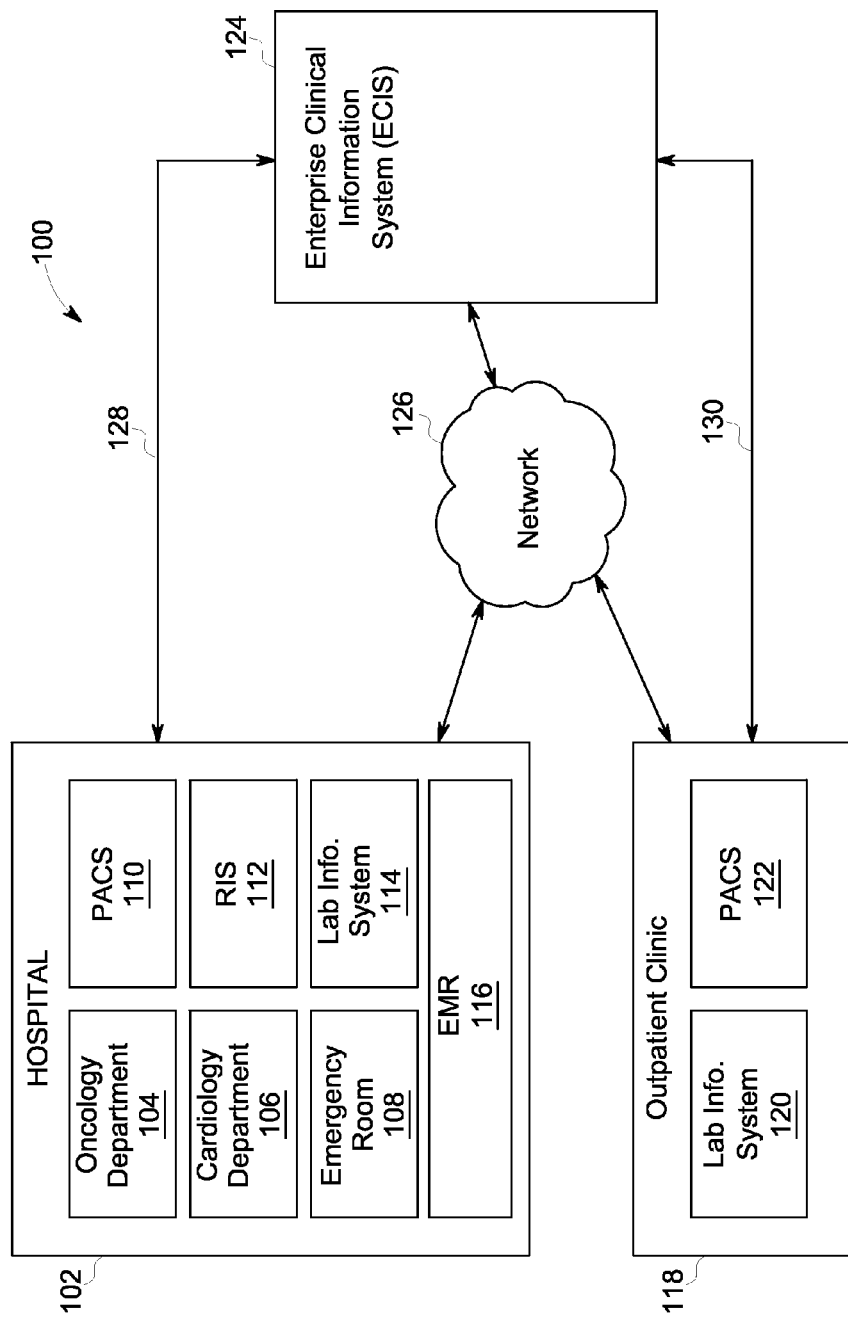
FIG. 1 is a block diagram of an example healthcare environment in which the example methods, apparatus, systems, and/or articles of manufacture disclosed herein for clinical content-based healthcare may be implemented.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in an embodiment, at least one of the elements is hereby expressly defined to include a tangible medium such as a memory, DVD, CD, Blu-ray, etc., storing the software and/or firmware.

Certain examples provide context-aware levels of detail to a clinical user. Certain examples provide a link of rich, reusable clinical capability between one or more clinical databases and/or other data stores and one or more clinical users.

I. Clinical Models

Detailed clinical models (DCMs), such as Clinical Element Models (CEMs) developed by Intermountain Healthcare, can be utilized as the basis to model, store, and/or retrieve dynamically changing clinical concepts and information.

A DCM, such as CEM, is a data structure that represents a unit of medical information, including its interrelated components. DCMs enable content-driven systems development so that healthcare delivery can be documented consistently, measured reliably, and improved continuously over time and across patients, providers, care settings, and applications.

Entities of healthcare enterprises operate according to a plurality of clinical workflows. Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, and/or any other action useful in processing healthcare information. The defined clinical workflows can include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

However, the entities of a healthcare enterprise and/or entities from separate healthcare enterprises sometimes operate within a broader, interdependent information system, which hinder the ability of entities to customize clinical workflows. For example, the information system to which a healthcare entity belongs may place restrictions on changes to workflow applications or programs. Moreover, because some healthcare entities operate using systems, programs, devices, etc. from varying manufactures, software providers, etc., a lack of interoperability between the systems, programs, devices, etc. of each healthcare entity prohibits many customizations from realization. As a consequence of these example factors as well as additional or alternative factors, healthcare entities that desire customized clinical workflows are typically required to request such customizations from the manufacturers, software providers, etc. Furthermore, for such customizations to implemented or integrated into a healthcare information system, a wide range of system-interrupting updates or re-releases occur within the information systems.

Certain examples provide a clinical knowledge platform that enables healthcare institutions to improve performance, reduce cost, touch more people, and deliver better quality globally. In certain examples, the clinical knowledge platform enables healthcare delivery organizations to improve performance against their quality targets, resulting in better patient care at a low, appropriate cost.

Certain examples facilitate better control over data. For example, certain example systems and methods enable care providers to access real-time patient information from existing healthcare information technology (IT) systems together in one location and compare this information against evidence-based best practices.

Certain examples facilitate better control over process. For example, certain example systems and methods provide condition- and role-specific patient views enable a user to prioritize and coordinate care efforts with an institution's agreed upon practice standards and to more effectively apply resources.

Certain examples facilitate better control over outcomes. For example, certain example systems and methods provide patient dashboards that highlight variations from desired practice standards and enable care providers to identify most critical measures within the context of performance-based care.

Certain examples leverage existing IT investments to standardize and centralize data across an organization. In certain examples, this includes accessing multiple systems from a single location, while allowing greater data consistency across the systems and users.

In certain examples, an advanced Service-Oriented Architecture (SOA) with a modern technology stack helps provide robust interoperability, reliability, and performance. The example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more IT systems and facilitate comparison(s) against evidence-based best practices. Certain examples provide one or more dashboards for specific sets of patients. Dashboard(s)

can be based on condition, role, and/or other criteria to indicate variation(s) from a desired practice, for example.

Generally, the example methods, apparatus, systems, and/or articles of manufacture disclosed herein enable healthcare entities of an enterprise clinical information system (ECIS) to dynamically customize one or more clinical workflows. Among other functions and/or benefits, the ECIS supports healthcare practitioners in decision making processes by aggregating healthcare information across disparate enterprises and/or entities thereof and referencing collection(s) of data (e.g., guidelines, recommendations related treatment and/or diagnosis, studies, histories, etc.) to automatically generate supportive information to be communicated to one or more healthcare practitioners related to the aggregated healthcare information. While each entity operates in connection with the ECIS that is administered by a provider thereof, the examples disclosed herein enable each entity of operating in connection with the ECIS to originate and/or modify one or more clinical workflows without relying on the provider of the ECIS to do so on behalf of the entity. In other words, although a healthcare entity is part of the ECIS and exchanges data with and via the ECIS, that entity can independently create and/or manage its clinical workflows using the examples disclosed herein. Furthermore, the examples disclosed herein enable entities of the ECIS to deploy or initiate the customized workflows without having to reboot or significantly interrupt the ECIS and/or the other components, workflows, etc., thereof. The example methods, apparatus, systems, and/or articles of manufacture disclosed herein and the advantages and/or benefits thereof are described in greater detail below in connection with the figures.

FIG. 1 is a block diagram of an example healthcare environment 100 in which the example methods, apparatus, systems, and/or articles of manufacture disclosed herein for clinical content-based healthcare may be implemented. The example healthcare environment 100 of FIG. 1 includes a first hospital 102 having a plurality of entities operating within and/or in association with the first hospital 102. In the illustrated example, the entities of the first hospital 102 include an oncology department 104, a cardiology department 106, an emergency room system 108, a picture archiving and communication system (PACS) 110, a radiology information system (RIS) 112, and a laboratory information system (LIS) 114. The oncology department 104 includes cancer-related healthcare practitioners, staff and the devices or systems that support oncology practices and treatments. Similarly, the cardiology department 106 includes cardiology-related healthcare practitioners, staff and the devices and/or systems that support cardiology practices and treatments. Notably, the example oncology department 104 of FIG. 1 has specifically designed clinical workflows to be executed in response to certain events and/or according to a schedule. At the same time, the example cardiology department 106 of FIG. 1 has specifically designed clinical workflows to be executed in response to certain events and/or according to a schedule that differ from the clinical workflows of the example oncology department 104 of FIG. 1. For example, the oncology department 104 may execute a first set of actions in response to receiving a Healthcare Level 7 (HL7) admission-discharge-transfer (ADT) message, while the cardiology department 106 executes a second set of actions different from the first set of actions in response to receiving a HL7 ADT message. Such differences may also exist between the emergency room 108, the PACS 110, the RIS 112 and/or the accounting services 114.

Briefly, the emergency room system 108 manages information related to the emergency care of patients presenting at an emergency room of the hospital 102, such as admission information, observations from emergency examinations of patients, treatments provided in the emergency room setting, etc. The PACS 110 stores medical images (e.g., x-rays, scans, three-dimensional renderings, etc.) as, for example, digital images in a database or registry. Images are stored in the PACS 110 by healthcare practitioners (e.g., imaging technicians, physicians, radiologists) after a medical imaging of a patient and/or are automatically transmitted from medical imaging devices to the PACS 110 for storage. The RIS 112 stores data related to radiology practices such as, for example, radiology reports, messages, warnings, alerts, patient scheduling information, patient demographic data, patient tracking information, and/or physician and patient status monitors, as well as enables exam order entry (e.g., ordering an x-ray of a patient) and image and film tracking (e.g., tracking identities of one or more people that have checked out a film). The lab information system 114 stores clinical information such as lab results, test scheduling information, corresponding practitioner(s), and/or other information related to the operation(s) of one or more labs at the corresponding healthcare facility. While example types of information are described above as being stored in certain elements of the hospital 102, different types of healthcare data may be stored in one or more of the entities 104-114, as the entities 104-114 and the information listed above is included herein as non-limiting examples. Further, the information stored in entities 104-114 may overlap and/or be combined into one or more of the entities 104-114. Each of the example entities 104-114 of FIG. 1 interacts with an electronic medical record (EMR) system 116. Generally, the EMR 116 stores electronic copies of healthcare records associated with, for example, the hospital 102 and the entities 104-114 thereof.

The example healthcare environment 100 of FIG. 1 also includes an outpatient clinic 118 as an example of another healthcare enterprise. The example outpatient clinic 118 of FIG. 1 includes a lab information system 120 and a PACS 122 that operate similarly to the corresponding entities of the example hospital 102. The lab information system 120 and the PACS 122 of the example outpatient clinic 118 operate according to specifically designed clinical workflows that differ between each other and the clinical workflows of the entities 104-114 of the hospital 102. Thus, differences in clinical workflows can exist between the entities of a healthcare enterprise and between healthcare enterprises in general.

In the illustrated example of FIG. 1, the hospital 102 and the outpatient clinic 118 are in communication with an ECIS 124 via a network 126, which may be implemented by, for example, a wireless or wired Wide Area Network (WAN) such as a private network or the Internet, an intranet, a virtual private network, a wired or wireless Local Area Network, etc. More generally, any of the coupling(s) described herein may be via a network. Additionally or alternatively, the example hospital 102 and/or the example outpatient clinic 118 are in communication with the example ECIS 124 via direct or dedicated transmission mediums 128 and 130.

Generally, the ECIS 124 supports healthcare information processing implemented by systems, devices, applications, etc. of healthcare enterprises, such as the hospital 102 and the outpatient clinic 118. The ECIS 124 is capable of processing healthcare messages from different entities of healthcare enterprises (e.g., the entities 104-114 of the hospital 102) that may generate, process and/or transmit the healthcare messages differently and/or using different formats, protocols, policies, terminology, etc. when generating, processing, and/or transmitting the healthcare messages. Moreover, the example ECIS 124 of FIG. 1 supports healthcare practitioners in decision making processes by aggregating healthcare information across disparate enterprises and/or entities thereof and referencing collection(s) of data to automatically generate suggestive and/or definitive data for communication to one or more healthcare practitioners related to the aggregated healthcare information.

Certain examples provide a library of standardized clinical content and proven best practices. Over time, this "library" of content may expand as healthcare organizations add to their own content modules. Because the content is standardized it can be shared and leveraged among organizations using the library and associated clinical knowledge platform. The library and platform help enable organizations to share best practice content. Thus, certain examples provide a clinical knowledge platform that enables healthcare delivery organizations to improve performance against their quality targets.

In certain examples, a quality dashboard application enables creation of one or more dashboards based on the data/content most relevant to an organization at a given period of time. A clinical knowledge platform brings together real-time patient data from existing IT systems within an organization and allows for the comparison of this data against evidence-based best practices. The example quality dashboard application leverages the platform to enable personalized "Quality Dashboards" to be created for specific sets of patients, based on condition, role, and/or other criteria. Variations from desired practice will be highlighted on each dashboard, enabling care providers to ensure better clinical outcomes and enrich patient care.

Figure 2:
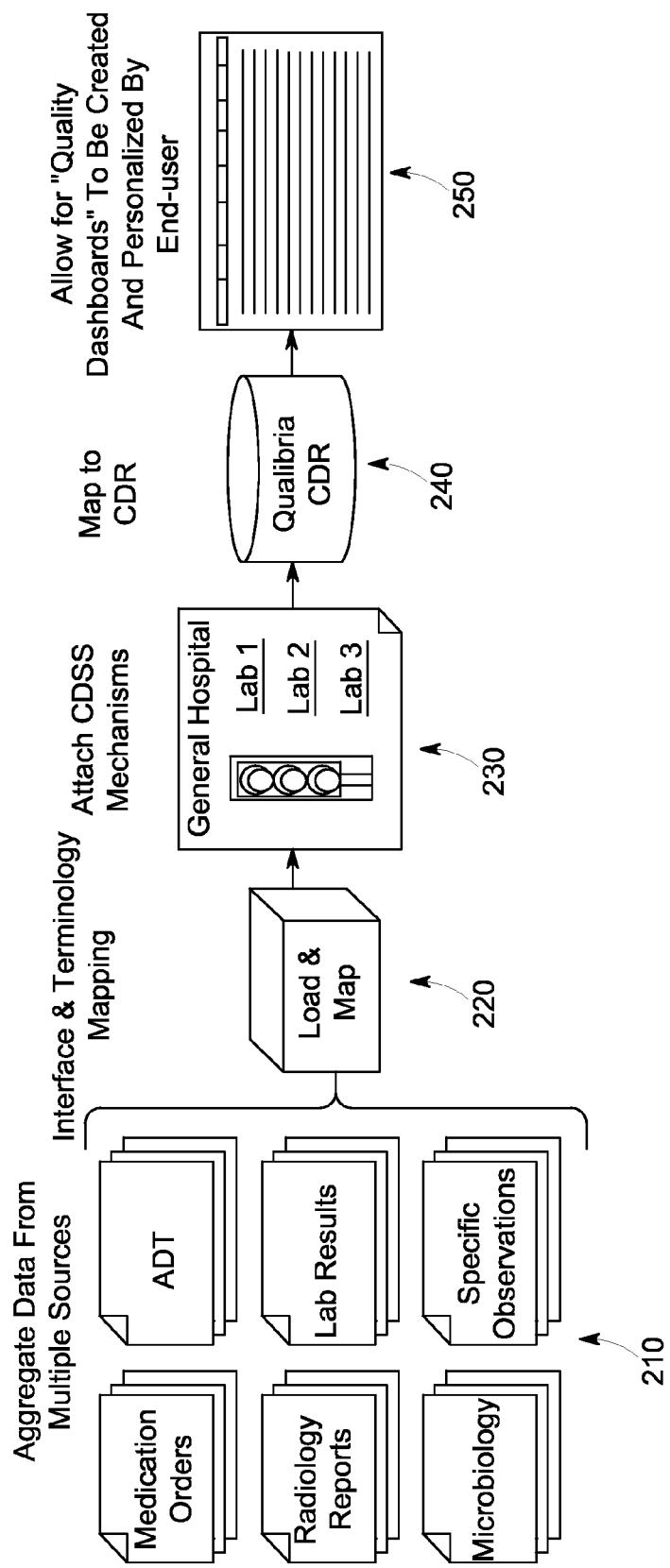
FIG. 2 illustrates an example clinical knowledge system providing an aggregation of data from multiple sources.

In this example, the clinical knowledge platform aggregates data from an organization's existing IT solutions. These can be solutions from the same and/or different manufacturer and/or provider. For example, as long as there is an HL7 or Web Services feed, the clinical knowledge platform can utilize the data from an existing solution. The existing IT solution(s) will continue to operate as they always have, and an organization can continue to use these solutions separate from the clinical knowledge platform if they so desire. However, the clinical knowledge platform and associated application(s) and/or workflow(s) can help to put organizations in greater control of their data by aggregating as much data from disparate IT solutions as possible. FIG. 2 illustrates an example clinical knowledge system 200 providing an aggregation 210 of data from multiple sources. Aggregated data may include, for example, medication orders, radiology reports, microbiology, admit/discharge/transfer (ADT) message, lab results, specific observations, electronic medical record (EMR) data, etc.

As the different data sources are pulled into a central data repository, content standardization occurs. It is this "standardization" that enables content from different IT sources to be used together. For example, as shown in FIG. 2, an interface 220 provides terminology mapping and standardization to the aggregated data.

After the content is standardized, clinical decision support mechanisms can be tied to the content (as illustrated, for example, by the clinical decision support 230 of the system 200 of FIG. 2). The data and associated clinical decision support are then stored in a clinical data repository (CDR), such as CDR 240 of the example system 200. By combining the aggregated and standardized data with clinical decision support rules and alerts, the clinical knowledge platform may provide end-users with an understanding of important elements to which they should pay attention (and take action on) within the larger set of data they are considering when caring for a patient.

Combined data and clinical decision support mechanisms create valuable content that, when arranged properly, may be used to improve the quality of care provided. Organizations can elect to use the application(s) that are provided as a part of the example clinical knowledge platform and/or may choose to build their own clinical application(s) on the platform. The open architecture nature of the platform empowers organizations to build their own vision, rather than base their vision on the static/hard coded nature of traditional IT solutions.

In certain examples, "Quality Dashboards" created via an example application display data via columns and rows in addition to individual patient "inspector" views. For example, the system 200 shown in FIG. 2 provides one or quality dashboards 250 to be created and personalized by an end user. The flexible nature of this dashboard application empowers organizations to create dashboards of the aggregated data based on their needs at a given period of time. The organization may determine what data elements they would like to include on each dashboard and, without significant IT resources, create a dashboard that reflects their vision. In addition, organizations can determine where on the dashboard they would like the information to be displayed and further adjust the view of the content via features such as "bolding" font, etc. When data is added to each dashboard, clinical decision support mechanisms attached to this data are displayed on the dashboard as well. For example, content related to treating a patient based on a particular use case may be included on a quality dashboard, along with alerts and notifications to indicate to end-users when desired outcomes are varying from defined clinical standards. Thus, organizations can create dashboards based on their own idea of "best practice" care for a given disease state.

In certain examples, since combined content and best practices have been standardized, content from one organization using the clinical knowledge platform may be easily shared with other organizations utilizing the platform. In addition, because the content within platform-related applications is standardized in the same manner, upgrades to the example platform can occur efficiently across organizations. That represents a dramatic change from prior IT solutions which require unique IT upgrades because they are usually uniquely customized to each organization in which they are installed.

Generally, content is information and experience that may provide value for an audience. Any medium, such as the Internet, television, and audio CDs, may deliver content as value-adding components. Content represents the deliverable, such as a DVD movie, as opposed to the delivery mechanism, a DVD player. As long as content conforms to the media standard, any compatible device can play it.

Content, as used herein, is the externalization or parameterization of "the instructions" that tell applications how to work. For example, content is a collection of externalized information that tells software, in conjunction with data, how to behave. In certain examples, a clinical knowledge platform takes in and executes content against data to render applications visually and behaviorally.

Content includes data read and interpreted by a program to define or modify presentation, behavior, and/or semantics of the program and/or of application data consumed by the program, for example. Content includes documents presented to a client by a program without modification, for example. Content may be created, stored, deployed, and/or retrieved independently of the creation and deployment of the program(s) consuming the data, for example. Content may be versionable to capture desired variation in program behavior and/or semantics, for example.

Classes of content may include configuration content, preferences content, reference content, application content, etc. Content types may combine behaviors of two or more classes, for example.

Software vendors take many different approaches to customization. At one extreme, some vendors write different software for each customer or allow customers to write software. At the other extreme, a vendor has the same software for each customer, and all customization occurs through creating or modifying content. In certain examples, the same software may be used for each customer, and customization is handled through content.

In healthcare, new laboratory tests, medications, and even diseases are constantly being discovered and introduced. Structuring this as content, where underlying software does not need to change, helps accommodate and use updated information.

In certain examples, many different content types, such as form definitions, data models, database schema, etc., are accommodated. In certain examples, each content type may be used differently and involve a distinct authoring tool. Thus, in certain examples, content may refer to "a collection of the content instances for all content types," also called a content repository, knowledge repository, or knowledge assets. For example, a content instance is a specific member of a content type, such as a heart rate data model.

In certain examples, each content type is associated with a generic, extensible structure that content instances of the content type follows. An example clinical information system can specify content in an abstract way that does not presuppose a particular software implementation, for example. That is, another system, such as GE's Centricity Enterprise, may consume content from a knowledge repository, apply a different set of software, and achieve the same behaviors. Additionally, an abstract content definition can more easily transition to a new system. If one can extract content from a legacy system, a knowledge repository may be able to import and reuse it. Such a capability helps reduce a large barrier to change for potential customers.

Content can change with time. In an example, a current knowledge repository can handle any "old" data entered into a system under the auspices of an older knowledge repository. Occasionally, a question may arise where someone could ask, "What did Dr. Smith see at some past time?" Under these circumstances, a current definition of a particular display may not correctly reflect the situation at the time. An example clinical information system (CIS), unlike other systems, can bring back the old form for visualizing the data since all knowledge assets are versioned and retained.

Content may need to vary for different circumstances. For example, a multi-patient view (MPV) may differ between emergency department (ED) and labor and delivery settings. Each MPV has rows and columns of data specific to its setting. Context refers to being aware of and reacting distinctively to a location and other situational differences. For example, interpretation of a patient's low temperature can vary based on location. If it occurs in the recovery room after cardiopulmonary bypass with deliberate patient cooling, it means one thing. If the patient is in the ED after breaking through ice into a lake, it means something completely different. Context may vary based on user location, patient location, user role, and/or various other factors. In certain examples, content may be applied based on context.

Globalization is a process of adapting software so that it has no language references, before embedding capabilities to make it suitable for particular languages, regions, or countries. Having globalized it, a CIS may then translate it to other languages and cultures, called localization. Globalizing a software product involves creating content separate from the software. For example, embedded text (e.g., user messages), sort orders, radix characters, units of measure, data formats, currency, etc., may be removed and parameterized. References to languages, character sets, and fonts may also be removed, for example. In certain examples, while display representations may be local, terminology concepts are applied universally, making a rule, calculation, or other content based on one or more terminology concepts useable worldwide without modification.

Figure 3:
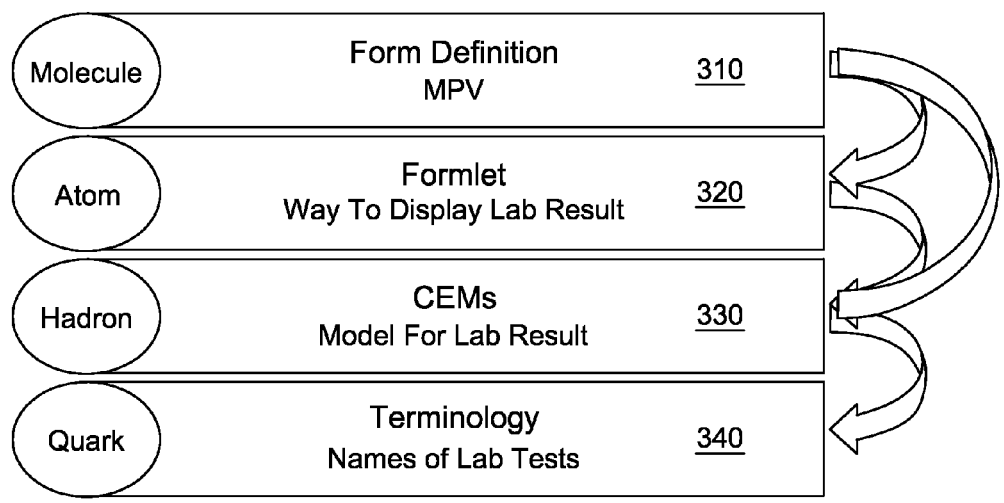
FIG. 3 illustrates an example interdependence of content types.

For example, FIG. 3 illustrates an example interdependence of content types. As shown in the example of FIG. 3, content is a set of interdependent building blocks. Content may be thought of as a hierarchy, with terminology 310 (e.g., names of lab tests) as a lowest level. Terminology 310 may be common and coded across a customer base. Clinical element models (CEMs) 320 govern structure and content of objects stored in a database and used by applications. A formlet 330 provides a way to display a particular content item (e.g., a way to display a particular lab result). A form definition 340 provides an application or view (e.g., a dashboard) of a collection of formlets (e.g., a multi-patient view (MPV) showing one or more lab results and/or other information). For example, if a particular MPV definition is moved from one customer to another, the MPV definition along with other content items on which the form definition depends are imported into the new customer's knowledge repository. Content items may include appropriate formlets, CEMs, and terminology, for example.

In certain examples, a detailed clinical model defines, at a granular level, the structure and content of a data element. For example, the detailed Clinical Model for "Heart Rate Measurement" dictates the data type of a heart rate measurement, and the valid physiologic range of a heart rate. It says that a "body location" is valid qualifying information about a heart rate measurement, but a "color" is not. It further decrees that the valid values for "body location" are terminology codes found in the "heart rate body location" value set. Moreover, it prescribes that a "resting heart rate" is an instance of "Heart Rate Measurement" where the value of "temporal context" is "resting", where "resting" is also a coded value. A detailed clinical model pulls the information together into a single, explicit, and computable form. The detailed clinical models or clinical element models (CEMs) govern the content and structure of all data objects stored in an example clinical database and used by applications, for example. In addition, CEMs are extensible, such that content authors may add new CEMs or attributes to existing CEMs without requiring major changes to database structures or software, for example.

In certain examples, shared or portable content is, in effect, "plug 'n play". System administrators can add it (e.g., plug it into) to a system without any software changes, and the content behaves in the intended way and does not cause errors. The size or scope of shared content can range from a single term to an entire knowledge repository, for example. Shared content fundamentally changes an implementation paradigm and reduces a total system cost of ownership, for example.

Customers can change shared content. Customers can improve it or make it more suitable for their institutions. When customers do this, they leave the original definition intact, but clone it and keep their changed version in their "local" space, for example.

As described above, classes of content may include configuration content, preferences content, reference content, application content, etc. Configuration content is content that is modified infrequently and is concerned primarily with system behavior, for example. Examples of configuration content may include internet protocol (IP) address and port of clinical knowledge database, identifiers of terminals in systems, security access privileges, configuration files, etc. Configuration content may affect program semantics, for example. Configuration content is generally modified by system administrators and is often stored in the file system, for example.

Preference content is modified frequently and is concerned primarily with variation between users. Examples of preference content include display colors and fonts, default search parameters, screen layout, etc. Preference content rarely affects program semantics and is most commonly modified by individual users. While modified by users, the system generally distributes initial or default preference content.

In certain examples, distributed or default preference content behaves very similar to application content before modification by a user. Preference content may be context sensitive, transformed at deployment, etc. Preference content may include vocabulary concepts and pick-lists that are resolved when loading and retrieving just like other content types.

Reference content is documents that are presented without modification as part of the application. Reference content is often stored in formats that are opaque to a program (e.g., as a portable document format (PDF) file, a Microsoft WORD™ document, etc.). Reference content is generally not specific to or customized for a specific patient (e.g., instruction sheets, information sheets, policies and procedures, etc.). Reference content may be independent of program semantics and behavior. Reference content may be authored independently of a program. While not an element of a content drive system per se, reference content is often managed as content by a clinical knowledge system. Once reference content is modified for presentation to a specific user, the content starts behaving much more like patient data/documents. Reference content with the structure to enable modification starts behaving much more like application content.

Application content may be modified frequently or infrequently depending on use. Application content may be concerned primarily with application behavior and semantics. Applicant content may be generally specific to an application domain. Examples may include a flow sheet template, clinical element models, terminology, document templates that are modified and stored as patient data (e.g., hot text), etc. Terminology is application content but has behaviors distinct from other application content types and is managed (largely) independently of other application content, for example. Application data often affects program semantics and behavior. Application content may be authored at multiple levels in an organization or external to the organization, for example.

Application content may be implemented as a custom markup language, for example. Application content may be implemented as a domain specific language (DSL), for example. For example, data queries may be implemented using a frame definition language (FDL). Clinical element models may be implemented using a constraint definition language (CDL). Application content may be directly authored or imported as data into a content store (e.g., concepts in a vocabulary server), for example.

In certain examples, while patient data is transactional and often includes discrete data elements, application content is often structured, complex objects and often has associated metadata. In certain examples, metadata is data used to manage content, such as content identifier, version, name of author, access privilege, encryption certificate, etc. Metadata is not treated as content, for example. While patient data is owned by a patient and is part of a legal record, application content is not owned by a patient and is not part of a legal record. Application content may be published (e.g., is not transactional) and managed using a lifecycle.

Certain examples provide content-driven systems and processes that rely primarily on content to determine application behavior. An example system includes a reference platform that consumes, interprets, and/or executes content while remaining application neutral. An example system uses content that remains independent of an implementation of the reference platform to allow independent evolution of the platform and the application.

Figure 4:
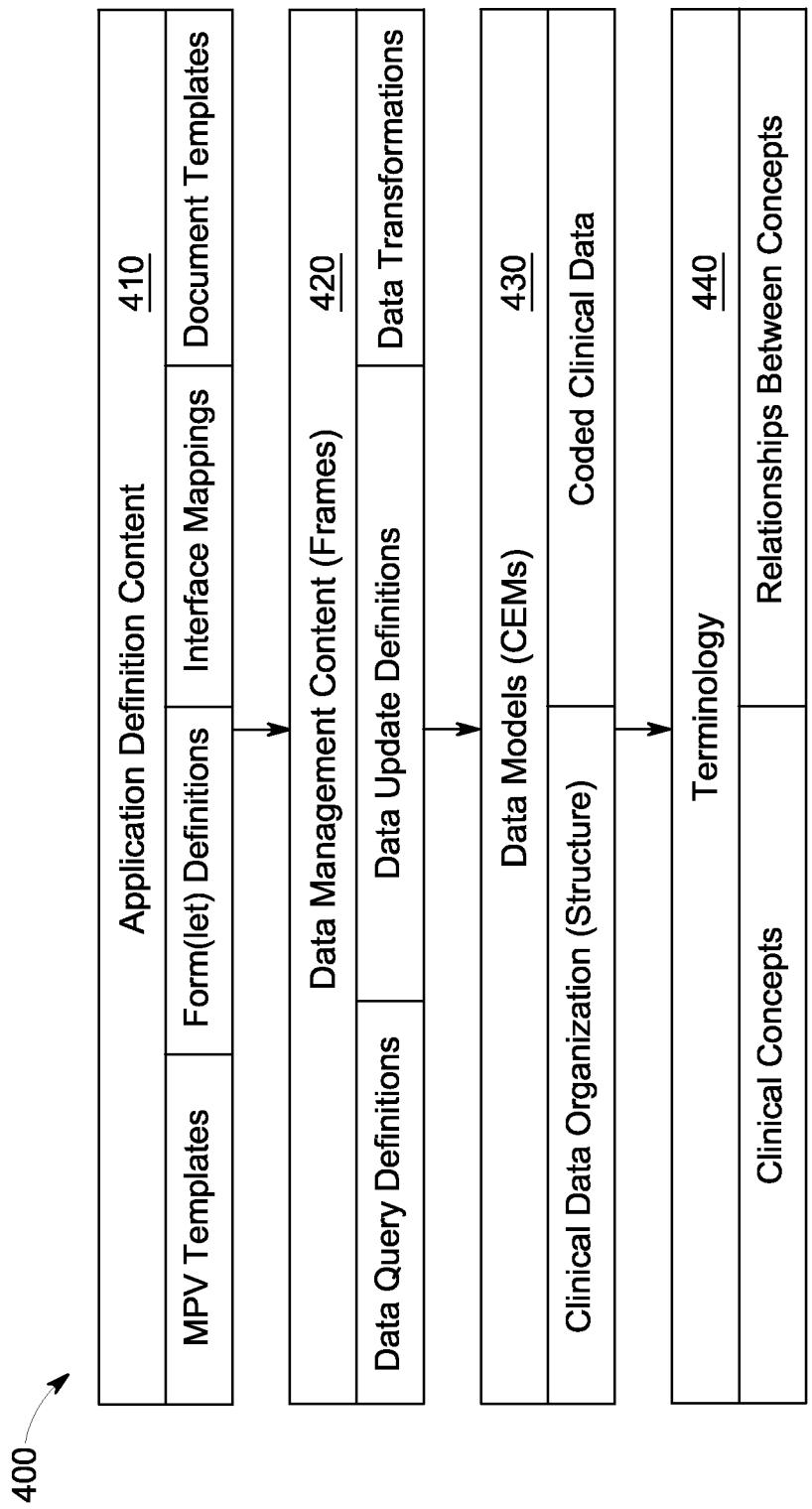
FIG. 4 illustrates an example hierarchy of content, associated data models, and terminology.

FIG. 4 illustrates an example hierarchy 400 of content, associated data models, and terminology. In certain examples, once one chooses content based data models, content-based queries and data management are also selected. Content based applications are also chosen. An integral terminology basis includes semantics of data defined in terminology content, for example. As shown in the example of FIG. 4, application definition content 410 (e.g., MPV templates, form(let) definitions, interface mappings, and/or document templates, etc.) relies on data management content (e.g., frames) 420 (e.g., data query definitions, data update definitions, and/or data transformations, etc.). The data management content 420 leverages data models (e.g., CEMs) 430, such as clinical data organization (e.g., structure) and/or coded clinical data, etc. The data models 430 are constructed based on a terminology 440 including clinical concepts and relationships between concepts, for example.

In certain examples, context refers to metadata attributes and/or labels that differentiate variations of a content item. For example, each variant of content item may be referred to as a context variant. Each variation of a content item has a specific set of context attributes (e.g., language, location, role, etc.). An algorithm or heuristic may select a desired variant when retrieving based on a current user's "context." This process may be referred to as context resolution.

Searching refers to examining the content item and/or associated metadata for matches independent of context. Searching can include context attributes to filter for specific context variants in the search. The difference is that a specific variant is not selected algorithmically or heuristically by the content system when searching. Using the "user" as a context attribute is one way to associate a content item with a specific user; similarly provider as a context variable could be used to associate an item with a group of users. Resolving context generally requires some heuristic to resolve ambiguity or conflicts among context variants (e.g., weighting or priority schemes, default rules, etc.). This leads to some ambiguity since changing/adding a context variant or changing the weights of context attribute may change the context resolution on another item in not always obvious ways (at least to a user).

In certain examples, a content item includes:

1. A root content item represented by a universally unique identifier (UUID). The root content item includes metadata only; no actual content is stored.

2. One or more context variants that represent variations of an implementation of the content item in different client contexts occur as children of the root content item.

3. Context variants may form trees of increasing context specialization (e.g., a context variant may have child variants).

4. Each context variant has a unique UUID as well as a relation to the root content item.

5. Each context variant maintains versions of that variant as changes are applied to the variant.

Figure 5:
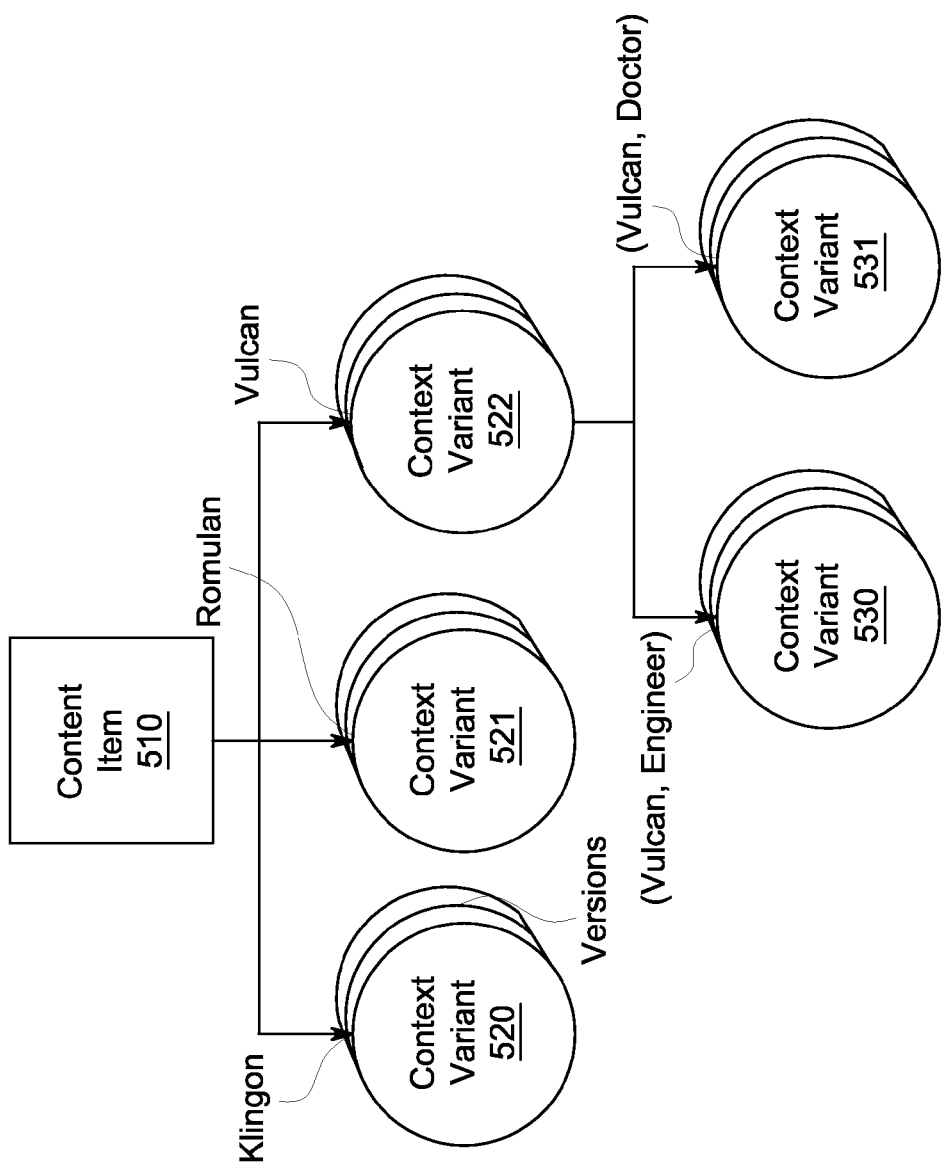
FIG. 5 shows an example root content item having one or more content variants associated with one or more context variants.

As shown in the example of FIG. 5, a root content item 510 has one or more content variants 520-522. Each content variant 520-522 may be associated with one or more context variants 530-531.

Figure 6:
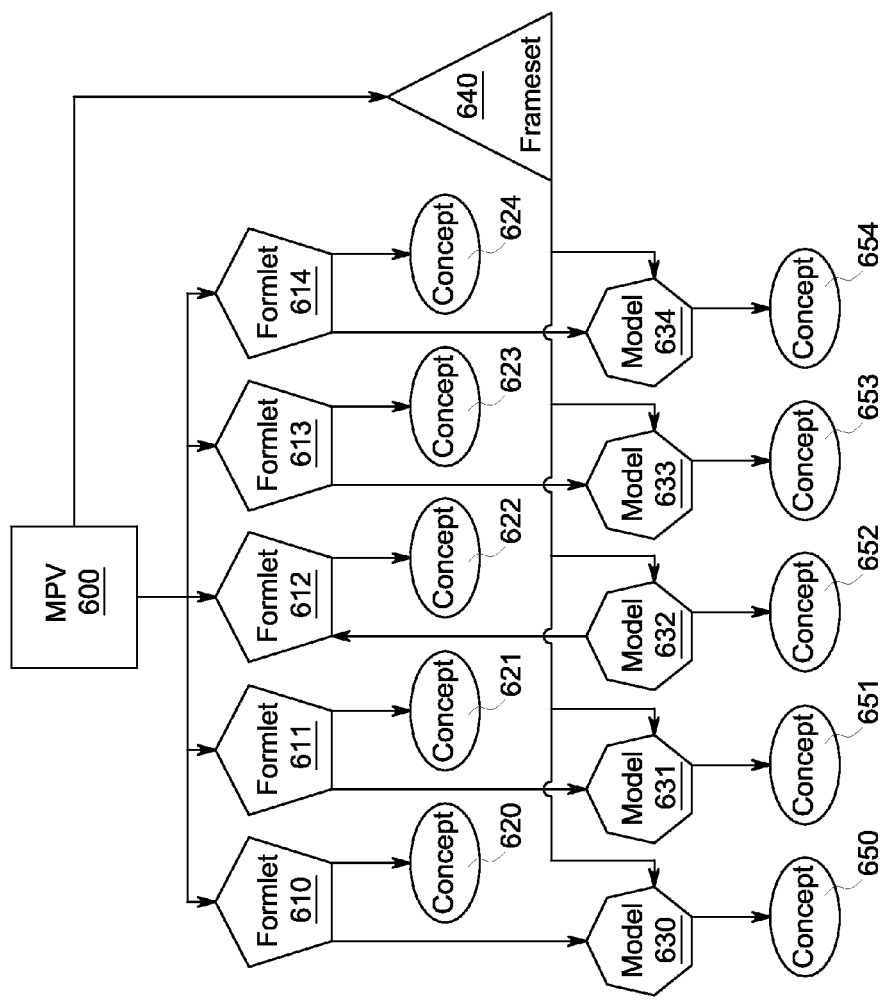
FIG. 6 provides an example multi-patient view made up of a plurality of formlets and a frameset.

FIG. 6 provides an example multi-patient view (MPV) 600 made up of a plurality of formlets 610-614 and a frameset 640. Each formlet 610-614 corresponds to a concept 620-624 and a model 630-634. The frameset 640 is also associated with each model 630-634, and each model 630-634 is associated with a concept 650-654, for example.

In certain examples, content may be stored in multiple content stores. For example, content may be stored in an ECIS database, an XDS repository, a third-party system, etc. Content documents in storage may be identified by a URI that specifies the content store and the key of that item in that content store. A content directory including the content metadata may be searched to obtain the URI for retrieval of the content item. A content type manager may specialize the search, storage, and/or retrieval of items of that content type, for example.

A content item in the content directory is keyed via a UUID for the item. That UUID is not necessarily part of the uniform resource indicator (URI) that defines the storage location.

In certain examples, content items may be organized as a content type. A content type is a set of content items that are defined and managed using common definitions and methodologies (e.g., terminology, clinical element models, frameset definitions, etc.). Content types may have different behaviors, states, lifecycles, etc. Each content type may be managed by a specific content type manager, which is treated as a plug-in to a clinical knowledge platform and/or associated clinical information system, for example. Content types may be added by creating a new content type manager, for example.

Content type managers may interact with a content management framework by implementing a set of event handlers (e.g., package, deploy, retrieve, etc.). "Generic" content types (e.g., content types with no special behavior) may use a default content type manager. An owner of a content type is responsible for implementing an associated content type manager, for example.

In certain examples, during authoring (that is, before deployment), dependencies exist between content items. At runtime (that is, after deployment), dependencies exist between deployed forms of context variants. Dependents that exist during authoring may or may not continue after deployment. For example, terminology description and pick-list resolution are translations during loading and retrieving, not dependencies per se.

In certain examples, at runtime, dependencies are between deployed forms of context variants, not the context variants themselves. The deployed form of a context variant is a "content frame". At deployment time, it may be necessary to guarantee that the packages (e.g., terminology) that a package depends on are also deployed. Terminology dependencies may be inferred from terminology relationships and mappings and do not need to be explicitly tracked.

In certain examples, a content based system provides a capability to distribute content and content updates to external instances (e.g., test systems, quality assurance systems, customer installations, content patches (SPRS), etc.). An example distribution system provides a capability to distribute content items and associated dependent content items and/or insure that those content items already exist in the target system. For example, an FDL content item must have access to the clinical element types it references in order to process a frame query. The example distribution system may also facilitate an undo or reversal of installed content items that generate issues. Content may be distributed as large sets of items (e.g., during installation) and/or as individual items (e.g., bug fixes), for example.

Figure 7:
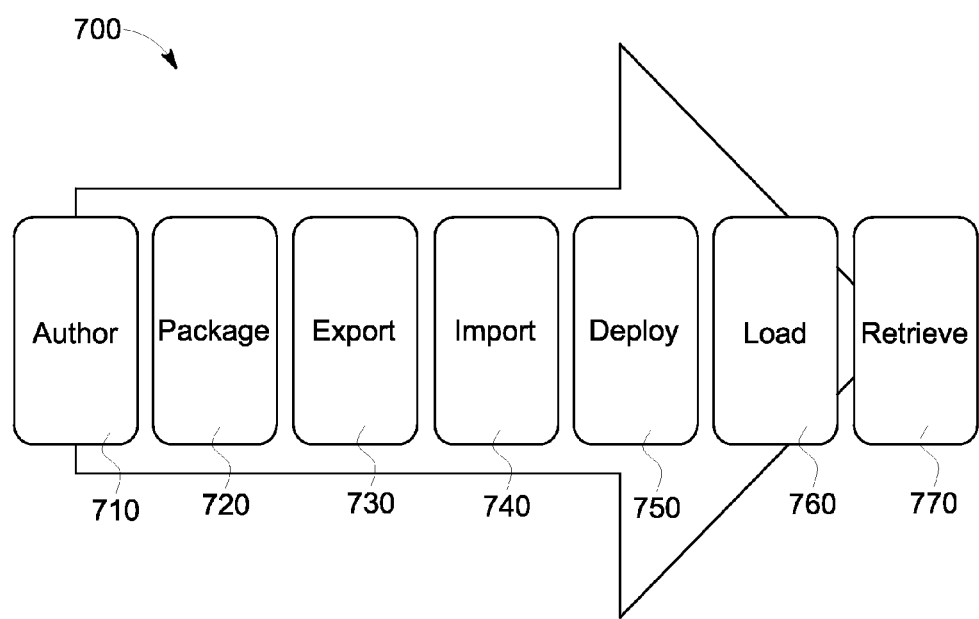
FIG. 7 illustrates an example content management process.

FIG. 7 illustrates an example content management process 700. The example process 700 includes authoring 710, packaging 720, exporting 730, importing 740, deploying 750, loading 760, and retrieving 770.

Authoring 710 includes a process of creating and/or modifying a content item. Authoring may be done by an author composing content directly using an editor (e.g., CDL, FLD, etc.), for example. Authoring may be done using tools (e.g., editor(s), etc.) that are specific to a content-type (e.g., terminology), for example. Authoring may be done by tools within the application(s) consuming a content type (e.g., MPV, forms, etc.), for example. Authoring may be done by applications generating a content item (e.g., MPV generating FDL), for example. In certain examples, there is no single authoring environment for content; rather, there is a family of authoring tools that is often content type specific.

Packaging 720 includes combining all content items and (applicable) context variants within a transitive closure of dependency graphs of one or more content items into a package, for example. Packages may include multiple independent top level content items, for example. Packages may have dependency(-ies) on other package(s). For example, a package containing a frameset content item may dependent on a separate terminology package as a prerequisite to deployment.

Packages may very frequently contain multiple independent, top level items each with its associated dependency graph. A package may not include all context variants of an item. For example, packaging may filter based on context to form a package. Packaging events may include an event to allow a content type manager to specify dependencies of an item being packaged.

Packages may have dependencies on content types other than content packages. For example, a terminology package is a different content type than a content package. Content items within a package may not have explicit dependencies on terminology concepts. Rather, the package has dependencies on the appropriate terminology packages.

In certain examples, packages are used as a distribution mechanism. Packages may be deployed before items in the package are available to a runtime system, for example. Packages themselves may be treated as content items. Thus, packages can themselves be packaged (e.g., packages of packages), and packages may be dependent on other packages. In certain examples, packages may belong to a namespace or domain. For example, packages may only include items from a single namespace. Packages may have dependencies on packages in another namespace, for example.

Package(s) may be exported 730 from one system and imported 740 into another. Exported packages may be used to distribute content, for example. System management tool(s) may be provided to create, export, import, and deploy content packages, for example.

Figure 8B:
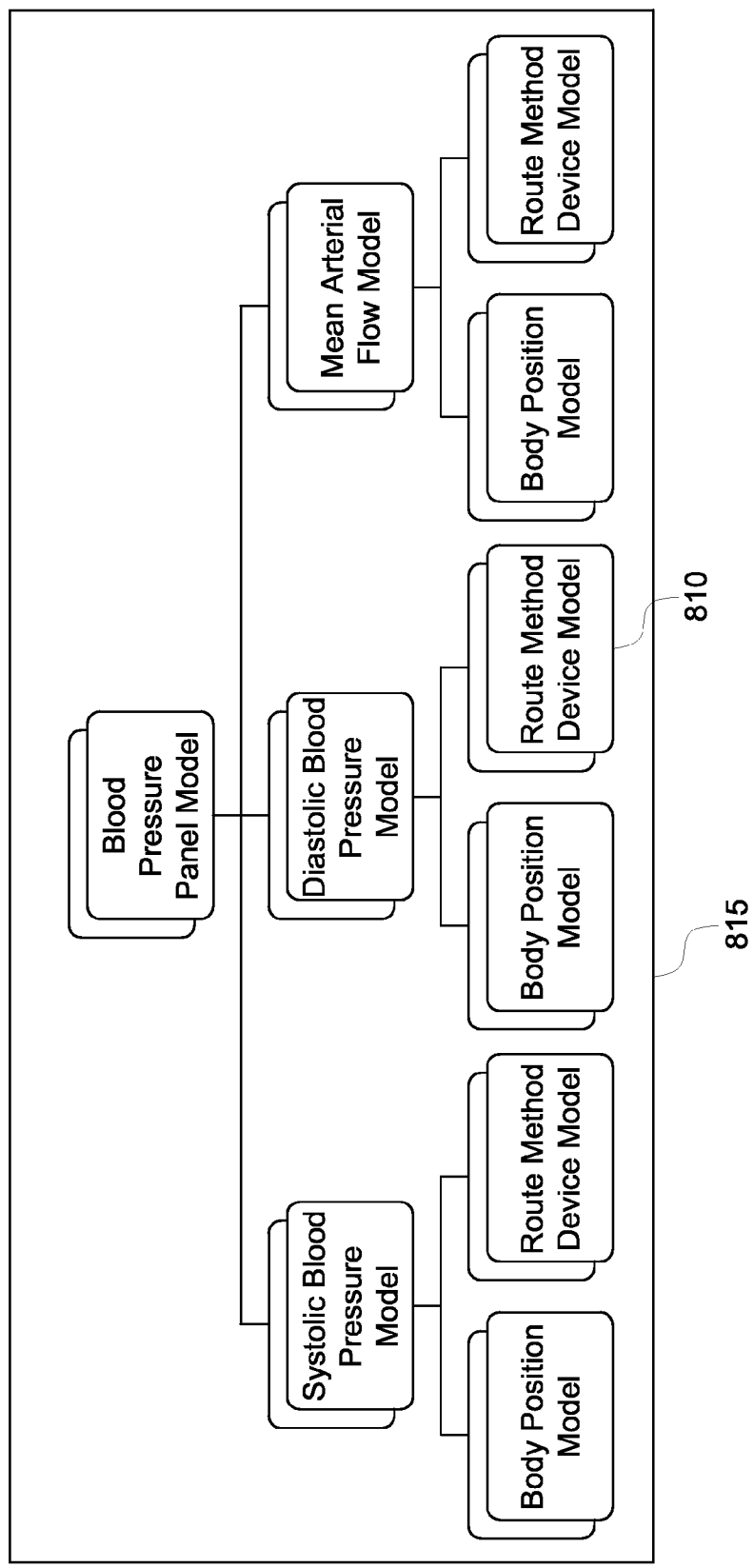
FIG. 8 shows an example deployment including a plurality of models in a content package deployed to create a content frame including plurality of type objects with associated schema.
Figure 8C:
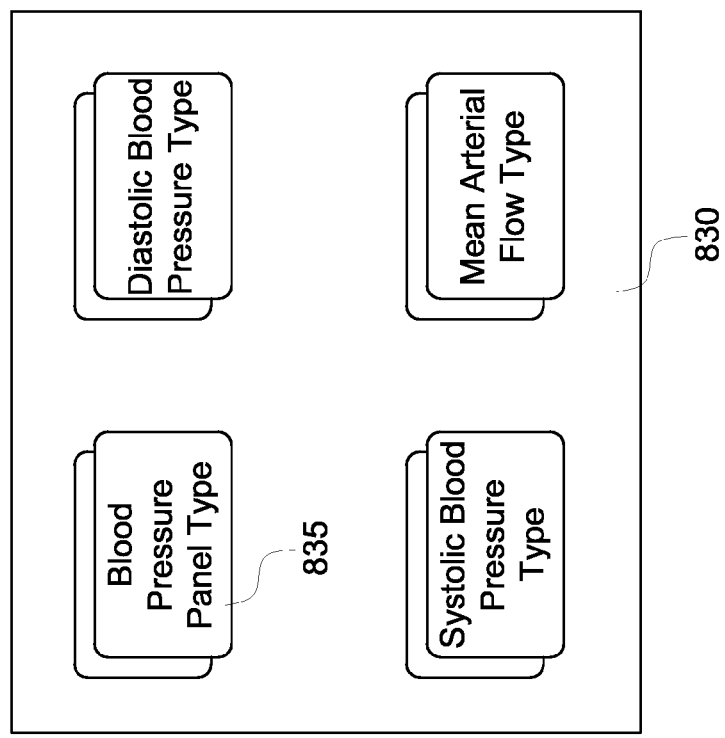

Deploying 750 includes making content items included within a package available to a running system. A content item may be transforming during deployment, for example. For example, constraint definition language (CDL) models may be compiled and may create multiple type objects each with an associated schema. As shown in the deployment example of FIG. 8, a plurality of models 810 in a content package 815 are deployed 820 to create a content frame 830 including plurality of type objects 835 with associated XML schema.

In certain examples, each top level content item in a package being deployed is deployed independently. A deployed content item is logically (and often physically) a different object than the content item being deployed. For example, a deployed content item has independent state and lifecycle. Multiple content items may be created during deployment, for example. For example, deploying a CDL model may generate a CE type object and an XML schema. In certain examples, a source content item may not exist in the runtime system. For example, the source CDL models are not employed, and the generated CE type object is deployed. Deployment of a package may be done manually and/or implicitly by an authoring tool, for example. For example, system administrators may wish to explicitly control deployment of data models but MPVs authored by a user may be implicitly and immediately deployed.

In certain examples, each deployed content item is bundled with all of the content items that are used to execute and/or consume the item. The bundle is referred to as a content frame 830. A content frame 830 is analogous to an archive file manifest. It may not (necessarily) contain the actual content items. The content frame 830 may not include all of the items generated during deployment. For example, the CDL schemas may not be part of the frame.

A content frame 830 is also analogous to a context variant. The frame has its own unique identifier but may be retrieved using the identifier of the root content item the frame is based upon in the same way that context variants are retrieved. Deployment events may include an event to allow the content type manager to specify dependencies of the deployed item(s) within the content frame, for example.

In certain examples, context resolution refers to conditioning selection, composition, and/or behavior of a content item based on a context of a user. Context resolution may occur at one or more levels. For example, context resolution may occur on selection of the content item(s) that a content item being deployed is dependent upon based on context. Such resolution occurs during deployment, and content frames are context specific with dependencies resolved. Context resolution may occur on selection of a content frame based on context when the content frame is retrieved by an application, for example. Context resolution may occur on translation of a content item based on context when loading and/or retrieving a content frame, for example. For example, context resolution may occur upon retrieval of terminology concept designations and/or retrieval and population of pick-lists.

Translation may be performed by the content type manager during loading and/or retrieval, for example. A template tool such as Apache Velocity may be used to implement the translation. The sensitivity of a content item to changes in the terminology server is a function of when the translation is applied e.g., during deployment, loading, or retrieval), for example. During deployment, context may be used algorithmically/heuristically to select dependent items and/or the deployment tool may specify the required dependent items. In general, context resolution is done heuristically (e.g., scoring and weighting schemes) because of the difficulty in determining an unambiguous algorithm to resolve conflicts. The content type manager may provide its own mechanism for context resolution, for example.

In deployment 750, a content item may be a part of multiple content frames. For example, multiple copies of a content item may be loaded by an application if it loads multiple content frames containing the item. Applications may search for and retrieve content frames. For example, content management may load and cache content frames. In certain examples, authoring tools may retrieve content items directly. Running applications may retrieve content frames during execution, for example.

Context may be resolved while constructing a content frame. That is, selection of context variants on which the deployed content item is dependent is done during deployment, for example. Content frames may thus be context specific. During load and retrieve, context may be used to select a content frame, not content items contained in the frame, for example.

A content frame may itself be considered a content item. Thus, the content frame may be versioned, have associated metadata, etc. Since a content frame is a content item, packages of frames may be constructed and distributed content frames without the associated source content items, for example. In certain examples, content frames may contain content frames, allowing courser grained deploy and undeploy operations. In certain examples, optimizations to frame loading (e.g., loading a single copy of a common content item) may be done, if desired, using techniques such as reference counting, etc.

In certain examples, content frames are related to a deployed root content item in a fashion analogous to the relationship between context variants and the content item. For example, a content frame is identified by the same UUID as the root content item in the frame and shares the same directory metadata. Each content frame may have its own unique identifier that may be used as a reference. Each content frame may be context specific and may have multiple versions. In certain examples, only deployed content items have associated content frames. Because of this relationship, content frames may be treated in a directory as properties of a content item along with context variants, for example.

In certain examples, content may be undeployed. An undeploy is a process of a making a (deployed) content frame unavailable to a running instance, for example. However, data instances stored in a CDR may be dependent on the content frames used to create the data instances (e.g., clinical element (CE) types). As a result, a content frame, once deployed, may not be physically deleted from the clinical content system without compromising referential integrity, for example. Undeploy, then, may make a content frame invisible to subsequent searches and context selection. Through undeploy, a previous version of a content frame may then be once again visible to search and context selection, for example. In certain examples, an undeployed content item may still be directly retrieved using the UUID for the content frame.

In certain examples, content item translation refers to modifying a content item during loading and/or retrieval to make the content item responsive to changes in content items on which it is dependent without redeploying the content item. For example, terminology designations and pick-lists may change independently of the deployment of the content item. Content item translation may be a responsibility of a content type manager responsible for a content item. For example, translations that make sense for one content type may not make sense for another content type. Content item translation may be context specific, for example. Content item translations may be performed by inserting custom macros in a content item (e.g., at authoring time) and applying a template tool to execute the macro and perform the translation with the item is retrieved.

Content item translations may be fine-grained. For example, they do not change the structure of the content item but replace elements (e.g., labels, lists of labels, etc.) within the item. Course grained modification of content frames (such as re-resolving content items that the content item being retrieved is dependent upon at retrieval time) may be undesirable because they can lead to unpredictable changes to application appearance or behavior. Hence, these kinds of modification are restricted to occurring at deployment time. In certain examples, common tools may be used to perform translation of content items represented in XML or HTML. Apache's Velocity is used here as an example only. Dependencies for items that depend on translations may be managed by maintaining a content frame dependency on a content frame containing the items to be translated (e.g., a terminology content frame) rather than by maintaining specific dependencies, for example.

Loading 760 is a process of retrieving a content frame containing deployed content item(s) from storage and making the frame available for use by running application(s). Content items in a content frame may be translated during loading. For example, terminology designations may be resolved and/or pick-lists retrieved. A content frame may be cached after loading. Content items contained within a content frame may be loaded as a single operation, for example.

In certain examples, the choice of doing translation at retrieval time or load time is up to the content type manager. Translating at load time means that the cost of translation is amortized over multiple uses of the item; translating at retrieve time means that the item is more sensitive to context variation and changes in resolved content. A selection of translation time may be content type specific, for example.

Retrieving 770 includes fetching a loaded content frame by a consuming application. Content items within the content package may be translated during retrieval (e.g., resolving terminology designations, retrieving pick-lists, etc.). A loaded content package may be retrieved multiple times by different clients, for example. An application may choose to reuse (e.g., cache) a retrieved content package at its discretion. Content items within a content frame may be loaded as a single operation, for example. In certain examples, since a content item may be present in different content packages, different instances of an item may be translated using different context. For example, an application may show a content item in two different languages concurrently for comparison.

A choice of doing translation at retrieval time or load time may be made by the content type manager. Translating at load time means that the cost of translation is amortized over multiple uses of the item. Translating at retrieve time means that the item is more sensitive to context variation and changes in resolved content. A selection of translation time may be content type specific, for example.

Figure 9:
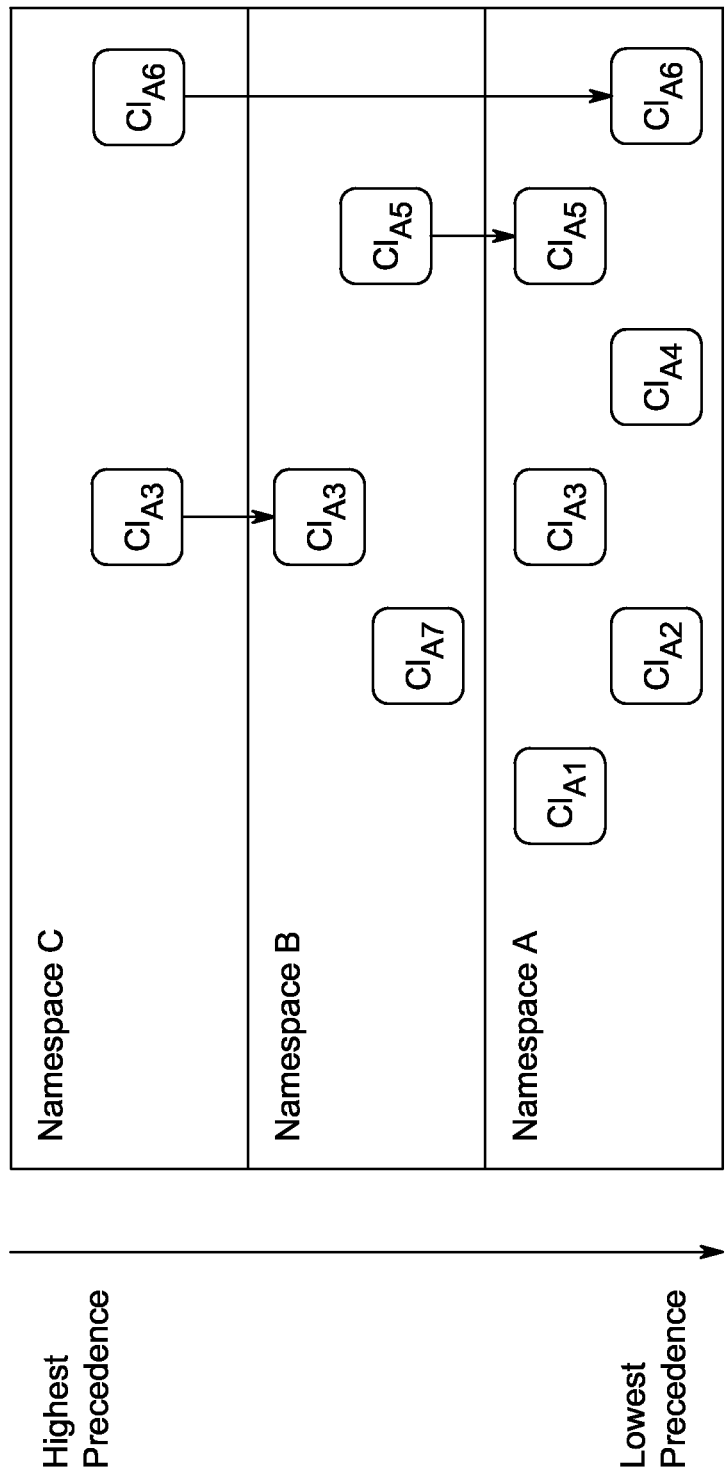
FIG. 9 provides an example of a plurality of namespaces including various content items.

In certain examples, content may be divided based on namespace. A namespace is a partition of content items in a system where each partition is owned and managed independently of other partitions. FIG. 9 provides an example of namespaces A, B, and C including various content items (CIs).

Namespaces may be motivated by various factors. For example, content items in one namespace may be protected from modification by another party (for example, a customer modifying GE distributed and owned content). Applying maintenance (e.g., updates, bug fixes, etc.) becomes difficult, if not impossible, if a customer can modify GE distributed content (e.g., customer modified content may potentially be broken when replaced with an update). Alternatively or additionally, for example, customers may be allowed to add and extend distributed content in safe ways while enforcing governance restrictions on such modification (e.g., models may not be modified or extended, but MPVs may).

While some of these restrictions may be enforced by a security system, customers often set security policy, so another mechanism may be used to enforce such restrictions. Additionally, some rules such as inheritance restrictions may not be adequately managed via security policy.

In certain examples, a simplified namespace model provides that each content item in a system may be searched for using a single namespace precedence order. It is possible that different content types may involve different search precedence (e.g., a search path to resolve data models may not be the same as a search path to resolve forms or reference content). Extensions to the model can be made based on circumstances, for example.

In certain examples, namespaces may be "owned" by a provider, a customer institution, a department, etc. Such ownership separates provider content from customer content, for example. Multi-tenancy and digital rights management may be facilitated through the use of namespaces, for example. In certain examples, only the owner of a namespace may create or modify content items within the namespace. An owner may own multiple namespaces, for example. A clinical knowledge platform and/or associated enterprise clinical information system may serve as an owner of a "root" namespace (and possible others), for example. Each customer installation may be an owner of at least one namespace for that customer, for example.

In certain examples, an "owner property" on a content item used as a context attribute is also presented in some contexts as equivalent to a namespace. However, in context resolution, using an owner property there may be no inherent precedence. For example, given a concept with designations potentially owned by A, B, and C, an application asks for the designation owned by A but that designation does not exist. Does the system return designation B or designation C? In general, property precedence in context resolution involves a heuristic to resolve (e.g., weighting and scoring schemes).

Additionally, there may be necessary relationships between content items in namespaces. For example, specialization via inheritance, overriding content items in one namespace with the same item in another, copying an item from one namespace to another (e.g., is it legal to do the copy?), etc. These behaviors may or may not be able to be implemented using an owner property (alone) in the general case.

Additionally, "owner" may be used in at least two different senses: first, as an intellectual property/digital rights management (IP/DRM) concept where it designates actual ownership (e.g., a package by "owner" is a practical application of this concept—package everything that is owned by an owner); second, as an attribute used to select a desired/appropriate context variant when retrieving a content item. This second usage is more directly analogous to namespaces with the caveats above.

In certain examples, a difference between an owner context attribute and a namespace is that namespaces are known to and defined by a system rather than defined independently for each content item in content (e.g., owners are generally terminology content). The system can establish precedence, maintain persistent/immutable relationships between items in different namespaces without expectation that the relationships will change, for example. That is, "namespaces" may be part of a reference implementation; owners are content defined and hence may be interpreted by the reference implementation, for example.

In certain examples, namespaces have "precedence" when searching retrieving, etc. For example, as shown in FIG. 9, a highest precedence namespace C is first searched for a content item, then a second highest (e.g., namespace B), etc. Precedence may be established when configuring the system or defining the name spaces, for example. Precedence may be overridden when deploying a package.

In certain examples, relationships may exist between content items in one namespace and content items in a lower precedence namespace. In certain examples, changing namespace precedence may change the nature of a relationship.

In certain examples, a new content item may be created in a higher precedence namespace by copying an item in a lower precedence namespace. For example, an MPV may be copied from base content, modified, and saved as a user-owned MPV. A content item may be created in a higher precedence namespace that hides or replaces the same content item in a lower precedence namespace, for example. For example, a new version of a formlet that hides the same formlet in base content to customize display of that formlet. Creating a new content item that specializes (e.g., inherits from) an existing content item may hide or replace a base content item in a lower precedence namespace. For example, a new attribute may be added to a patient clinical element model provided by specializing the patient model.

In certain examples, namespace relationships are managed by a content management system. If a base content item is modified, a specialized content item may need to be redeployed. In certain examples, specialization of a content item in a namespace may be allowed in another namespace but copying the content item may not be allowed. State changes in a base content item may involve state changes in a specialized content item (e.g., if the base item is deprecated, the specialized item may also require deprecation), for example. In certain examples, digital rights management may prevent a copy of a content item from being created. In certain examples, if a content item that was copied to a new namespace is modified, an owner of the target namespace may need to be notified of the change so the copy can be reviewed for changes.

In certain examples, an owner attribute on a content item may be insufficient to manage namespace relationships. Clinical element models (CEMs) are an example of a relationship restriction: copying and hiding a CEM can lead to data inconsistencies while specialization through restriction or extension can be safely done. Hiding an MPV on the other hand, is generally a safe operation, for example. In certain examples, relationship management/enforcement is a responsibility of a content type manager (CTM), or at least the CTM should be able to specialize system relationship management.

Namespaces may be used in a variety of stages of a process. For example, namespaces may be used during authoring. For example, namespaces may be used when resolving context variants, establishing relationships such as copy, copy and hide, etc. Namespaces may be used during packaging, for example. A package may include content items from a single namespace, for example. Context variants, relationships, etc., in other namespaces involve dependencies on packages in those namespaces, for example. Namespaces may be used during deployment (e.g., when resolving context variants, when establishing relationships such as inheritance relationships, etc.), for example. In certain examples, namespaces are not used during load and retrieve at runtime.

In certain examples, each context variant of a content item has a current "state". For example, a state may include deployable, deployed, loaded, deprecated, etc. Each content type has a set of allowable states and a set of allowable state transitions represented as a state machine. Content types may have different state machines in an authoring environment than in a runtime environment, for example. State machines may be owned by a content type manager since the manager defines a meaning of each state for a content type.

In certain examples, a state in a runtime system is actually the state of the content frame. However, for simplicity, a state of the content frame is assumed to be (and managed as) the state of the root content item. A state of content items included via dependency resolution may be irrelevant to the runtime system (e.g., it may be required that the root content item of the content frame be redeployed to bubble up state changes in that item).

In certain examples, lifecycle management refers to a set of workflows that manage transition of a content item from one state to another. Each state in a content type state machine is associated with a distinct workflow that manages the content item when in that state, for example. In certain examples, workflows are content items to allow variation across implementations.

II. Clinical Element Query Language, Systems, and Methods of Use

In certain examples, a query language based on clinical element models (CEMs) is provided for querying data based on CEMs and relationships that are part of the CEMs. As described herein, a clinical element query language (CEQL) is a language for expressing model-specific queries. Since there are no physical structures with CEMs and relationships are meta-relationships in an object, there needs to be a mechanism to express the meta-relationships in a query. Rather than querying physical structures, CEQL is used to query logical structures found in objects based on CEMs. Since CEQL is clinical element model-centric, CEQL is implicitly aware of relationships between models. A frame defines a collection of data, and frameset is a set of those collections. Frames are defined via queries, including CEQL queries and transform queries. For example, a programmer writes CEQL queries to define frames to construct forms (e.g., applications). In certain examples, a CEQL query result is a tree of objects that is navigable via the CEQL.

Current clinical application and forms efforts involve much customization and hardcoding of fields, data, operations, etc. A change in an application or form similarly involves an extensive manual effort and potentially a significant time lag. By providing a clinical element query language to standardize, simplify, and streamline interaction with underlying clinical element models and associated data, application and forms generation, customization, and use can be improved.

In certain examples, a user can build models and build queries for the models using CEQL. A resulting frame structure is returned. The frame is a result set. A CEM gives relationships between objects that are returned. For example, in a lab panel, objects for results and relationships between results (e.g., objects) are defined, and a lab panel can include many patients and keep track of which labs are owned by which patients. A frame specifies relationships between objects and who owns the objects. That is, a frame serves as a container that knows how to hold objects and relationships between objects. A user or program can put as much information as desired in a frame and write the frame to a database or other data storage as a single unit. CEQL, for example, is a language used to define contents of frame. A Clinical Element Transformation Language (CETL) operates on content of frame and turns the frame into something an application can execute or use.

In certain examples, CEQL provides a language for expressing model-specific or model-centric queries. For example, using CEMs, models are provided with metadata such that a single object is provided at runtime with one or more models used to understand and interpret contents of the object. Relationships can be defined as meta-relationships in an object, for example. CEQL can be used to form a query including one or more objects and relationship(s) (e.g., meta-relationship(s)) between objects. For example, objects may not be aware that they are part of a collection (e.g., an encounter). A query can be formed using CEQL to retrieve a lab panel and all of its result objects including relationships between the objects, for example.

For example, a user (e.g., a human user and/or automated program) can construct and/or trigger a query to, for example, retrieve all patients that are on the fifth floor of a hospital as well as all chemistry labs (if any) for each patient. In certain examples, the query is a functional language query that, rather than querying physical structures, is querying logical structures that are found in the objects. The language itself (e.g., CEQL) knows what it means to be on the fifth floor, for example.

Continuing the example, from p in Patient, e in Encounter can be joined using p where e is assigned a location as department equals five 5. Then, 1 in chemlabs can be joined using p, and p,1 is selected by the query. Thus, a location is treated as a department and a patient bed is internally translated to a department. This query with joins represents an implicit relationship that is carried over into a frame to allow a user to navigate them at runtime, for example.

Thus, certain examples provide a query language that is model centric in which the query language implicitly is aware of or has information regarding relationships between models. A query can be composed, and an output is, for example, a Structured Query Language (SQL) output for that query. Once a result set is identified, objects can be filtered in different ways.

In certain examples, queries are used to populate frames in a form. A frame can be defined via the query. When defining a frameset of frames, a human and/or electronic user is actually defining a set of queries. In certain examples, a CEQL query result is a tree of objects that is put into a frame, and the CEQL allows navigation of the object tree. CEQL queries can be written by a programmer to define frames to construct forms, for example.

Certain examples provide a query generator to generate queries (e.g., a query for labs, a query for blood pressure, etc.). In certain examples, a query can be a combination of a plurality of sub-queries such that a single query of a database, rather than a plurality of separate queries, retrieves the requested information. The query generator takes requests and assembles them into a single query which is turned into a SQL query which provides requested terms or information, for example.

In certain examples, a grammar is defined and tested to generate results on artificial clinical data repository (CDR) data.

In certain examples, a query can be parameterized (e.g., rather than fifth floor, can ask for patients on a current floor and pass in a location L and a department floor=$L to act like parameterized stored queries). Queries can be compiled when they are built, and a resulting content item contains the compiled query and is executed at runtime. Thus, a query can be stored as a content item for later use by a system, such as a clinical information and/or clinical decision support system, for example. In certain examples, CEQL and CETL are used with frames to provide a frame definition language (FDL).

III. Clinical Element Transformation Language, Systems, and Methods of Use

The Clinical Element Transform Language (CETL) is a language for taking results returned by a query and translating them into a form that is useful for an application. Transforms are targetable to different applications, for example. Customers build models and build queries for the models using CEQL, and results are provided as a frame structure. The frame is a result set. A CEM gives relationships between objects that are returned. For example, in a lab panel, objects for results and relationships between results (objects) are provided, and a user can have many patients and keep track of which labs are owned by which patients.

A frame gives relationships between objects and who owns the objects. That is, a frame serves as a container that knows how to hold objects and relationships between objects. In certain examples, there is no limit to an amount of information to put in a frame. CEQL is a language used to define contents of a frame. CETL operates on content of frame and turns it into something an application can do. The frame can be written to a database or other data store as a single unit, for example.

In certain examples, data can be transformed structurally and/or semantically. The CETL facilitates transforms with respect to a query constructed using CEQL. Transforms result in a data graph of objects, for example. In certain examples, CETL includes two parts—a navigation language and an emit language. CEQL and CETL together with frames provide output, for example. Formlets operate over the output of the transforms, for example.

In certain examples, CETL serves as a bridge between 1) queries for clinical element models built using the CEQL and 2) a resulting frame and/or formlet to be used to form a presentation for an application. The transform enables associations to be made and relationships to be established. Additionally, CETL enables navigation of relationships and reduction or avoidance mix-ups and confusion between objects, for example.

Certain examples provide flexibility to separate the transforms and relationship resolution from the query defined using the CEQL. Certain examples allow flexible, dynamic, easily customizable, yet structured, creation of forms and applications.

In certain examples, a transform language, such as CETL, provide a language for taking results returned by a query and translating them into a form that is useful for an application. The transforms are targetable to different applications.

In certain examples, customers build models and build queries for the models using CEQL. A frame structure is provided as a result of the query(-ies). The frame is a result set. A CEM gives relationships between objects that are returned. For example, in a lab panel, objects for results and relationships between results (objects) exist. Thus, many patients can be monitored along with which labs are owned by which patients.

In certain examples, a query result is provided as a data graph of a plurality of objects, wherein each object is also a data graph. A user (e.g., a software and/or human user) can navigate a tree of objects and, when an object is reached, a tree corresponding to that object is navigated. In certain examples, navigation includes a translation into an internal structure of an object. In certain examples, relationships (e.g., implied and/or explicit) can be navigated.

In certain examples, CETL is implemented as a declarative language for navigating framesets, frames, and instances. CETL can be used to extract discrete data for consumption by an application, for example. Data may be transformed (e.g., structurally). For example, data can appear to be a rowset in SQL (e.g., a standard SQL result set). For example, a multi-patient view application (e.g., frame views, a frame view is a result of this transform, etc.) can be formatted as one or more SQL rowsets so that the application can be displayed in a table.

Alternatively or in addition, CETL can be used to make results appear as simple objects (e.g., fact objects), such as an object with a plurality of attributes inside the object. In certain examples, pieces can be picked from the data graph to build a consumable fact object. In certain examples, data results can be provided to an enterprise data warehouse (EDW) via an extract, transform, load (ETL) process. For example, analytic tools in an EDW are relational. Data can be extracted from one or more CEMs and turned into a table row/column model to populate an EDW and/or another structural transformation, for example.

In certain examples, data can be transformed semantically. For example, terminology designation retrieval can be facilitated. For example, a word can be used as a synonym for a concept. However, the word is no longer the concept, so the concept cannot be retrieved using the word. The concept can be displayed, for example. In certain examples, one or more aggregation functions (e.g., give an average of values (e.g., average temperature over last 24 hours for a patient), see standard deviation, minimum, maximum, hourly lab values, etc.) which operate over sets of objects can be provided.

In certain examples, data quality issues can be addressed using CETL. For example, sometimes, inconsistent data types (e.g., a pH test gives back real pH number or a value on a relative scale (+1, +2, etc.)) can be addressed as part of the transform (e.g., provides an average plus an indicator of a value that is not part of the average that the user (e.g., a doctor) can drill down and see). In certain examples, such values and transform is provided in content, rather than code.

In certain examples, CETL includes two parts that are interleaved in the language: a navigation language and an emit language. The navigation language provides a mechanism to navigate a data graph to identify data of interest (e.g., to a program, user, etc.). The navigation language can operate by progressive set restriction, for example.

Using progressive set restriction, results can be viewed in a data graph as a set of objects. A certain set of objects is provided and then restricted further by traversing the data graph or tree to reach a certain level at which elements, and only those elements, found at that level in the tree can be operated on. In certain examples, no order is provided at a tree level unless imposed by a user (e.g., software and/or human user).

For example, a query may select p in Patients over F1 (e.g., select all patients in this frame, ignoring other things in the frame); emit p.name (patient identifier); select 1 in labs over p (take each patient one at a time and only deal with the labs that are owned by that patient); and emit 1.value (then get patient identifier and lab in resulting output).

In certain examples, each select takes a current set of objects and restricts it to a subset. Each object can then operate on each object in the subset and restrict further. A process can continue restricting until it obtains a desired value. Value(s) can be emitted at any point. Emitted values determine a form of output, for example. The structure of the emits defines what a resulting object looks like. In certain embodiments, a transform can be built, and the emits define the structure of the output. Certain embodiments facilitate navigation of the result set without data confusion or mix up (e.g., between patients).

The navigation language can be a declarative language, for example. Safe navigation is inherent in the language due to the structure of the language.

In certain examples, the emit language is used once data of interest has been found and transformed (e.g., a JAVA™ object populated with values in it). For example, with a multi-patient view (MPV) application, a row structure can be generated with extract, transform, load (ETL) to build an SQL table/row structure for the application.

In certain examples, the emit language is targetable. A system may have multiple emit languages for a single navigational language, for example. The emit language may be used to emit a Java object, a pseudo row set, a data stream, etc. The emit language can also call library functions (e.g., services, decision support, etc.) as a transform of data is being performed. Thus, a transform may include: decision support calls, application services, library functions, etc. For example, library functions can include calculations (e.g., glaucoma score because a user wants to show the computed score rather than the raw data so that is what is emitted as a result of that function; get lab result and get indicator of whether the lab result is normal/abnormal and indicate lab result and/or normal/abnormal; etc.). In certain examples, data error management/data error handling can be facilitated via the emit language and data transform.

In certain examples, CETL can be for visual (e.g., formlets) as well as non-visual transforms. Frames, CEQL, and CETL work together to build forms and/or other interfaces/applications. Formlets operate over the output of the transforms, for example. Formlets define what the transform is and then, at runtime, operate on the output of the transforms. Formlets are not tied to what the model is, but rather operate on the output of the transforms of the models.

IV. Systems and Methods for Organizing Clinical Data Using Models and Frames

In certain examples, customers build models and build queries for the models using CEQL. A frame structure is returned. The frame is a result set. A CEM or other DCM gives relationships between objects that are returned. For example, in a lab panel, objects are provided for results and relationships between results (e.g., objects). The lab panel results could have many patients and need or want to keep track of which labs are owned by which patients. A frame provides relationships between objects and who/what owns the objects. The frame provides a container that knows how to hold objects and maintain relationships between objects. In certain embodiments, there is no practical limit to an amount of information to be put into a frame, and the frame can be written to a database as a single unit. CEQL is a language used to define contents of a frame. CETL operates on content of the frame and turn it into something an application can do.

Frames define how data is organized. Otherwise, a clinical element model (CEM) is a collection of unorganized objects to be organized to make them useful. Frames define a transactional unit as a set of result objects with relationships in the transactional unit. Frames provide a "safe" navigational mechanism through the results data. Frames manage a set of clinical element instances and relationships. Frames can be grouped into collections called framesets and define operations between frames, supporting parallel and partitioned queries, for example.

Certain examples improves upon and eliminate a need for customized, hardcoded, dedicated application development and replace it with a more flexible, adaptive and yet structured, platform using clinical element models, data, queries, and transforms with frames. Certain examples provide dynamic, adaptive, content-based organization and presentation of information and functionality.

Frames define how data is organized. A CEM is a collection of unorganized objects that are to be organized to make them useful. For example, a runtime for clinical element (CE) instances is provided. An instance is an instantiation of a CEM. Instances can be placed into a frame, and the frame is submitted into a database and/or other data store. Sets of CE Instances can be organized and relationships between objects can be managed, for example. Ownership can be preserved along with associations (e.g., panels), groupings (e.g., encounter membership), etc.

A transactional unit (e.g., lab panel (e.g., CDC)) can be defined as a set of result objects. Objects as well as relationships between objects can be written, and the relationships are not necessarily structural (e.g., may or may not have a pointer from one object to another so frame helps maintain that relationship). Result objects and relationships can be written as a single transactional unit, which is nice from a service-oriented architecture (SOA) standpoint because single internet transaction can occur.

Figure 10:
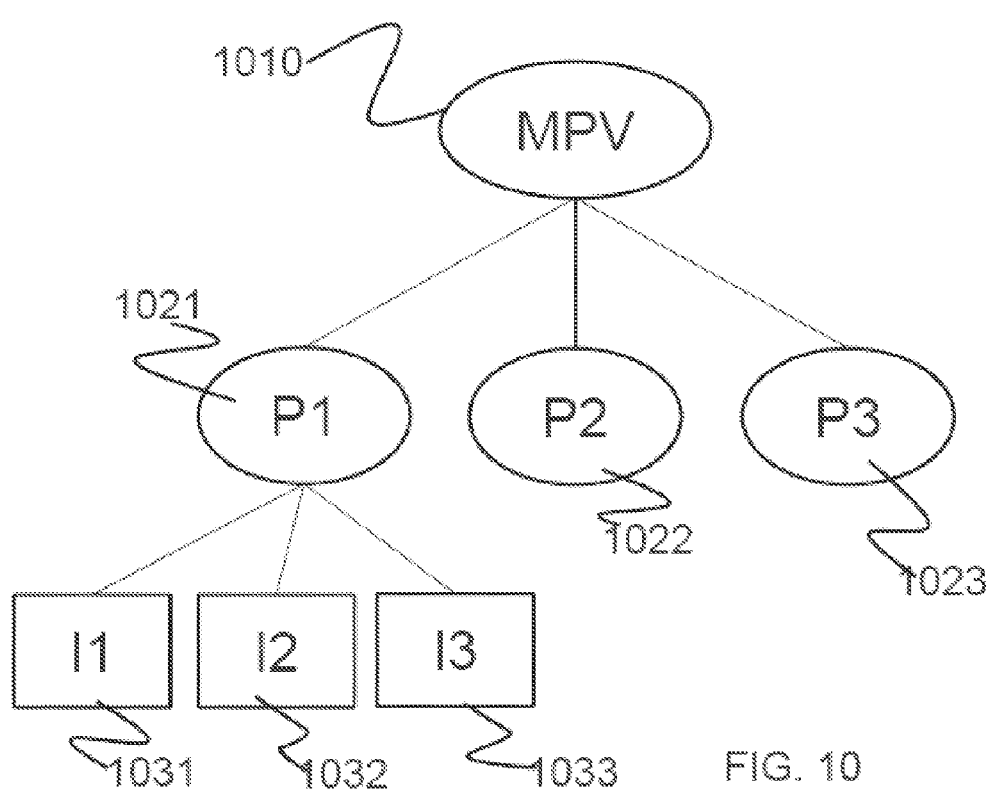
FIG. 10 illustrates an example multi-patient view application including a plurality of patients and objects.

Using the emit language provides a "safe" navigation mechanism. For example, when building an MPV and executing a query to populate a frame with data for 50 patients, a user wants to guarantee that data is not mixed up. For an MPV application 1010, such as illustrated in the example of FIG. 10 with patients P1, P2, P3 1021-1023 and objects I1, I2, I3 1031-1033, the user wants to ensure instance I1 1031 is not associated with P2 1022. Retrieving objects out of a frame for P1 1021 and then looking at the instances/objects 1031-1033 associated with P1 1021 makes it less easy for someone to make mistakes and get a patient hurt through an incorrect or unintended association.

In certain examples, "cursors" define a position in a result set as the result set is navigated and can be used to allow a user (e.g., human and/or software) to only navigate particular paths in the result set. Result sets and their relationships can be managed as a single closed object, for example. Result sets can be grouped into collections called framesets. Operators between frames, such as union, intersection, etc., can be defined.

Figure 11:
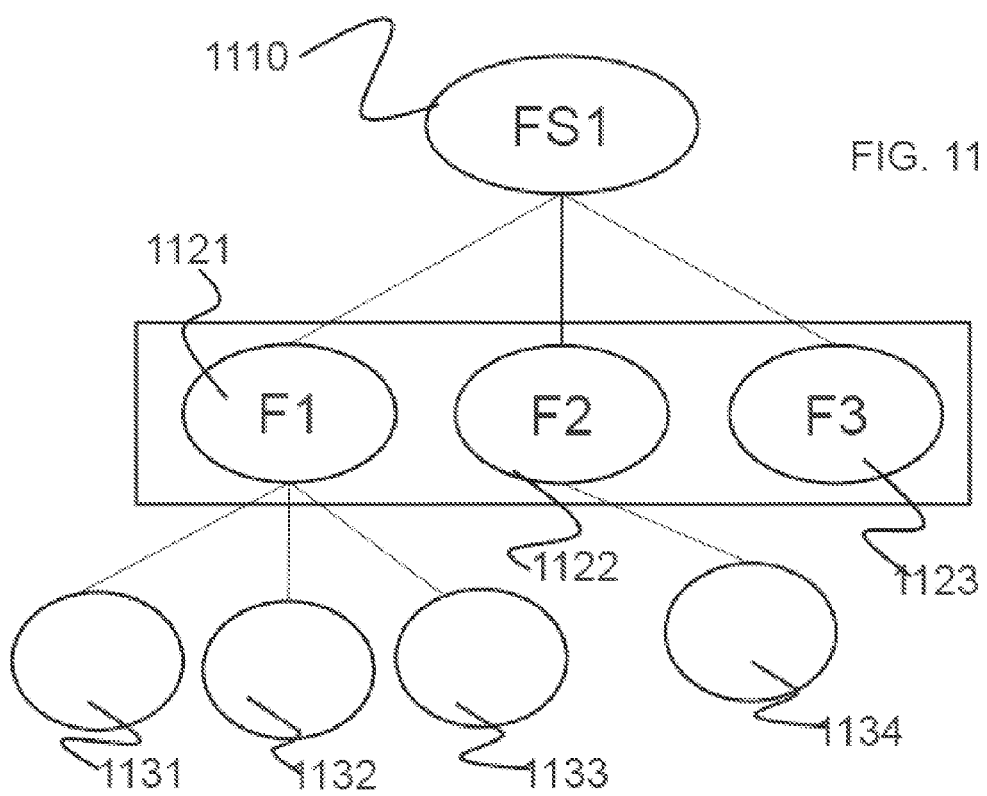
FIG. 11 depicts an example frameset including a plurality of frames.

For example, FIG. 11 depicts an example frameset 1110 including a plurality of frames F1, F2, F3 1121-1123. Each frame 1121-1123 can include one or more objects 1131-1134.

In certain examples, parallel and/or "partitioned" queries are supported. For example, an MPV includes a list of patients that are "favorites" for a particular physician. The physician is in a unit, so the physician may want to also see patients in that unit. Additionally, a patient list is provided in an electronic medical record electronic health record system such as GE's CENTRICITY™ Enterprise that the physician wants to use because he's covering for another doctor. Thus, when the system refreshes there are three queries to perform. Three queries are performed and a union is taken of the results to identify the target patient set. Once the patients have been identified, data for those patients is gathered. The three queries may be executed in parallel and unioned because a patient may show up in multiple lists/queries. A partition allows multiple targets for queries (e.g., different systems). Results are returned and perhaps additional operations can be applied to those results. Framesets allow operations to be applied to multiple sets, multiple frames, etc. A frame defines a collection, and frameset is a set of those collections. An application is provided through a meta-organization of objects (CEMs) with operators applied to or otherwise associated with them, for example.

In certain examples, CEQL, CETL and frames combine to form a frames definition language (FDL). An FDL generator generates frames using CEQL and CETL, for example. The FDL generator takes snippets of query(-ies) and combine them to get a query and a transform and in turn build a content-based application, such as a multi-patient viewer. CEQL leverages CEMs/DCMs, and frames allow a user (e.g., software and/or human) to use CEQL to use and consume CEMs/DCMs.

V. Frames Definition Language

In certain examples, a content-based system includes a content-based data definition. Using a content-based data definition, data definitions can change even after the system is compiled. An application can be generated to write a new object of a given (but changing) type to a database and can then query that object across system releases and updates. In certain examples, the query is expressed as content apart from a schema so as not be tied to a particular database schema which may change. Thus, a reference layer can change but the content layer is stable for users.

Certain examples provide a language to define queries against a content-based data item (e.g., queries include update and create commands). A translator is provided to interpret a language and turn the language into an SQL query for a reference platform.

In certain examples, query predicates are built against a model for content. Queries are made in reference to clinical element models. An interpreter converts queries into locations based on the clinical element models. Objects are provided as hierarchical data structures. CEMs and/or other DCMs can be used to express hierarchical queries based on an understanding of data organization and storage in a system, for example.

Once hierarchical data objects have been retrieved, the retrieved objects are transformed into a form consumable by a requesting application. As part of the transformation, data variability and other issues are treated. Using an application-specific data format, a transform is defined by how the particular application expects the data. For example, a query is defined, and then a transform is defined on top of the query. The query and the transform are tightly coupled, so they can be put into one language and then further defined by the application. A frames definition language, for example, can be formed using two languages—a transform language and a query language. The transform language deals with data variability by treating all data as sets and performing progressive restrictions on sets until desired item(s) are identified. Variability can be introduced based upon a state of the data and how the data is being restored by the user. Data can include multiple representations, different data types, etc., the system and language(s) are to deal with the shape the data is in and utilize the data.

Thus, transforms can be defined in content while reducing or minimizing the ifs/exception (if this, do that, etc.). For example, an application can write a transform in FDL, store the transform in content, and compile the content, where the transform can be done at least partially in compile so that the transform does not have to be done at runtime. By performing a transform at compile time, optimization(s) can be applied that cannot be used at runtime.

In certain examples, a declarative, set-based restriction model is provided via a FDL. Using the declarative, set-based restriction model, an application can drill down to desired data to determine whether the data is present. If no data is present, an error does not occur, but, instead, a transform can insert a null value for the application to indicate that the desired data is not there.

In certain examples, a data write is an inverse of a data read. A transform of the data from its representation in the application to an expected representation for a data model is performed. Since there may be data variability, certain data may or may not be present, and the transform can reflect a presence or absence of certain data without transmission loss. Thus, a transform is to structure the data to make the data computable without fidelity loss even though an application may not be able to tell if it has all the pieces expected. Using content and data models, an interface is viewed as an application and behaves no differently than a data entry form, which provides flexibility in application generation and execution and data transformation, for example.

In certain examples, a user is provided with tools and syntax to express a query and transform in an FDL or component (e.g., CETL and/or CEQL) of the FDL. In certain examples, one or more languages work with one or more data information models to provide relationships between pieces of data (e.g., clinicians communicating with each other to provide comments indicating relationships between pieces of data in a chart). Each item (e.g., note, image, report, etc.) is a data model. The model can be extended to include annotations (e.g., a relationship between 1 to N data items to allow an annotation to define relationships between data). For example, a lab result is an annotation defining relation between two other pieces of data.

VI. Systems and Methods for Formlet Generation and Presentation

In certain examples, a formlet is a presentation piece; a piece that describes a connection to models (e.g., formlets are bound to clinical element models (CEMs) to know what data elements to use), and sufficient information to generate a transform language and a query. A formlet represents a cell or a field on a form, for example. Formlets are independently authored and can be combined arbitrarily to generate a transform/query. For example, users can build models and build queries for the models using CEQL and receive in return a frame structure, where the frame is a result set. A CEM provides relationship(s) between objects that are returned. For example, in a lab panel, results are objects, and relationships between results (objects) can be provided. A user may have many patients, and, thus an application is to keep track of which labs are owned by which patients. A frame provides relationship(s) between objects and who owns them (e.g., serves as a container that knows how to hold objects and relationships between objects). As described above, CEQL is a language used to define contents of a frame, and CETL operates on content of a frame to transform the content into something an application can do.

Figure 12:
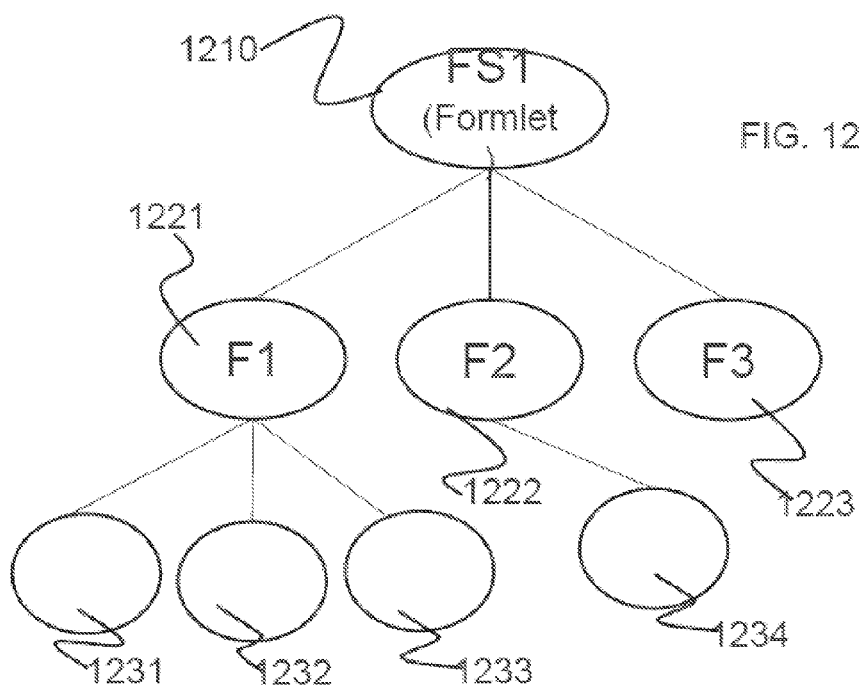
FIG. 12 illustrates an example formlet including a plurality of frames.

FIG. 12 illustrates an example formlet 1210 including a plurality of frames F1, F2, F3 1221-1223. Each frame 1221-1223 includes one or more objects 1231-1234.

In certain examples, a formlet has three components—a presentation component, a query component, and a translation component. In certain examples, all three components are to be specified for a formlet. In certain examples, a form element is not bound directly to a model but is instead bound to the model via a CETL transform. That decoupling provides greater flexibility, whereas direct binding can be too restrictive. In certain examples, formlets are made metadata-based to enable them to be used as a source form of a transform. Formlets and their underlying components/languages enable applications to retrieve and display data through generation of query and associated transform.

A user interface or displayed application view can be implemented as a collection of formlets, and each formlet can be composed of more formlets. For example, a lab summary formlet can include icons for each lab that can be implemented as independent formlets so that information about each lab result can be presently differently.

For example, a tree structure can be provided, where each element of tree has a bit of a desired query. At an end node, available formlets at that level are combined into a query snippet. The tree structure is traversed to move up the tree with a growing query/transform snippet of parent and child, taking each node and reducing it to a single node until the top of the tree is reached with a single composite query. At each level of the tree, a query and a transform for a desired formlet are generated. In certain examples, an FDL generator facilitates the tree-walking process to end up with a query and transform that can be expressed in FDL. For example, a single query and single transform representing a MPV are the output of the FDL tree structure navigation process.

Clinical applications today must be manually coded by skilled programmers. Customizations are time-consuming and usually involve consultation with the original provider to develop the customized version of the application. Using clinical element models, transforms, queries, and frames, customization can be dynamically facilitated by a user. Thus, certain examples provide dynamic, adaptive, yet structured construction of forms, interfaces, and other applications.

For example, query criteria inform what shows up on the rows of an MPV, such as which patients do a clinician want to see in MPV (e.g., all male patients, all patients in room 7, etc.). One or more query snippets (e.g., one or more CEQL snippets) are formed, where each query criteria has one or more snippets of CEQL. A formlet informs columns of the MPV, such as by specifying what data to show for those patients and how the data should be shown. Each formlet gives rise to a CETL snippet. A query is constructed from a family of CEQL snippets and a family of CETL snippets to retrieve data for a frame. The snippets are provided to the FDL Generator to form an FDL script. The FDL script has a CEQL section and a CETL section. Rather than forming a cohesive whole, CEQL snippets and CETL snippets are formed by the FDL generator into a CEQL query and a CETL query. The FDL generator provides an FDL script has one CEQL query and one CETL query. Data is then identified and retrieved and provided to the application for presentation and use.

For example, a desired data set can include patients (male or hypertensive) and in Room 7 (and/or other complex Boolean logic). Male is a first CEQL snippet, hypertensive is a second CEQL snippet, and Room 7 is a third CEQL snippet. The snippets are passed into the FDL generator as a tree. The FDL Generator takes the snippet tree and compiles to reduce and create an abstract snippet tree (AST). The AST is merged as specified by an associated predicate (e.g., OR, AND, XOR, etc.). CETL is similar in that it uses reducers, but the structure is a bit different. Instead of a tree, two lists (e.g., a top level snippet list and a referenced snippets list) are provided. Some example top level snippets include a patient name snippet, a lab collection snippet, etc. An example CETL snippet can be represented as follows:

```
CETL Snippet {
    itemCollection LabCollection
    from 1 in [type Lab] {
        [referenced snippet Lab]
    }}
```

Square brackets indicate that information is missing, and additional processing is to be before the snippet can be legitimate CETL, for example. The FDL generator looks for that snippet in the list and inserts the missing information (e.g., if it can be determined).

In this example, a collection of labs (a collection of type Labs) is being formed, and, for each lab in the collection, a referenced lab snippet is going to be processed.

```
CETL Snippet {
    item Lab {
        var labAlias = [type Lab]
        Attribute Name = labAlias.name;
        Attribute CollTime = labAlias.time;
    }
}
```

Thus, information in a Lab snippet is moved into to the LabCollection snippet of this example.

```
CETL View
    ItemCollection rows
    from p in Frame 1 {
        ItemCollection labCollection
        from 1 in p.FrameChildren (took type Lab and
        converted it to p.FrameChildren)
        item Lab
        Attribute Name - 1.name
        Attribute CollTime - 1.time
    }
}
```

The generator checks with a query to see if it supports that type and, if it does not, instructs the query to support that type. The query then determines a way to associate the type (e.g., type Lab to p.FrameChildren in LabCollection). Reference snippets are reduced into their parents (e.g., using AST), and type requirements are resolved by requesting the query to rearrange itself so that it is also requesting that requested type.

Figure 13:
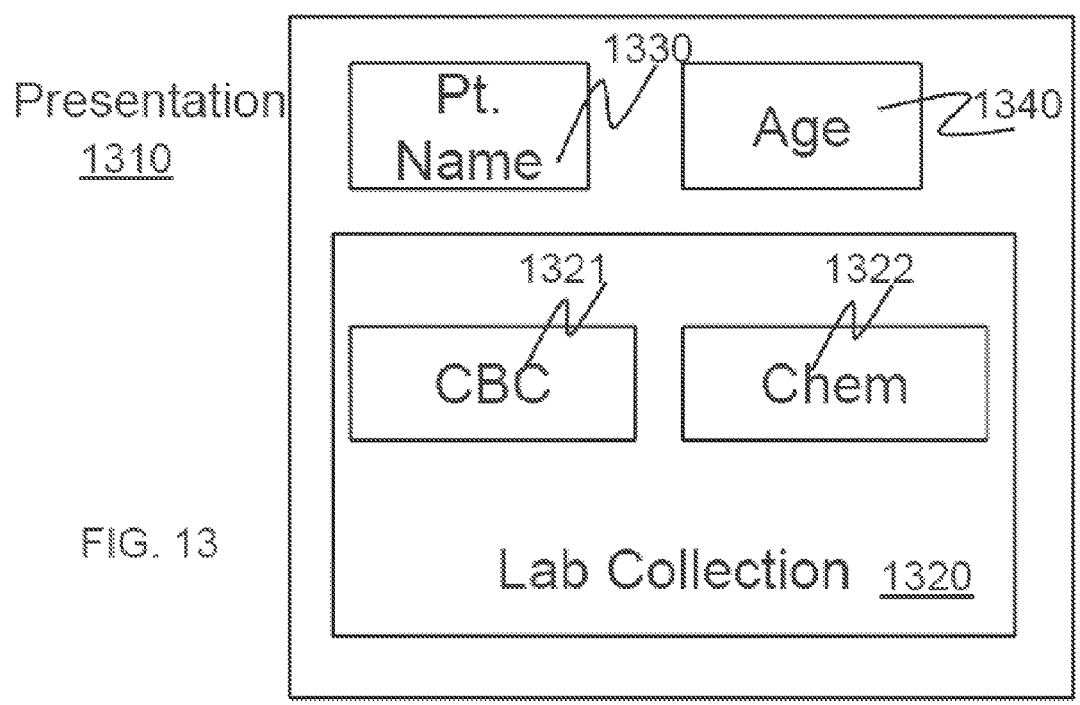
FIG. 13 depicts an example presentation component of a formlet.

FIG. 13 depicts an example presentation component 1310 of a formlet including a lab collection snippet 1320, a patient name snippet 1330, and an age snippet 1340. The example lab collection snippet 1320 includes a CBC snippet 1321 and a chem panel snippet 1322, for example.

In certain examples, an FDL Generator includes a CEQL generator and a CETL generator. The CEQL generator takes CEQL snippets, reduces them, and generates a final CEQL query. The query is passed to the CETL generator to compile each of the CETL snippets separately, reduce out the reference snippets (e.g., Lab), and then ensure that the query supports all the reference types in the CETL. The FDL Generator creates an FDL script with the CEQL query and the CETL query.

Then, the CEQL is passed through a CEQL compiler, and the CETL is passed through a CETL compiler. The output of the compilers includes transforms and a query. The transforms generated by the CETL compiler are code (e.g., JAVA™ code) which can then be compiled to class files and stored in content as class files. Then, when the transform is to be run, the class files are loaded (e.g., into a Java Virtual Machine (JVM)) and run. The query, when run, has, for example, SQL inside of it (e.g., the CEQL compile generates SQL). The SQL is run on a database to return a result set to be used to populate a frame in a hierarchical structure. The application requests that a particular transform be run on the view. For example, a first transform on an MPV is a top level grid, and a transform is applied to convert the grid into a data structure that is directly analogous to a desired presentation view.

A transform extracts information from a CEM and puts the information in an appropriate place in the MPV view based on one or more associated attributes. The transform provides a data object that the MPV application can consume. Rows and columns are bound to specified items, and the data populates the rows and columns for the MPV application display.

Thus, in certain examples, rather than hardcoding logic in an application, the application can easily leverage the underlying structure to create applications in a content-based format. Domain-specific compilers (e.g., CEQL, CETL) perform specific jobs and provide clinical configurability that clinicians want to customize applications.

In certain examples, CETL can be written to allow input of data into the system through a transform. A user can input data (e.g., a comment) and ensure sure the data gets into the right place (e.g., a CEM object with user context attached to a comment object, time of day, location, etc.).

Figure 14:
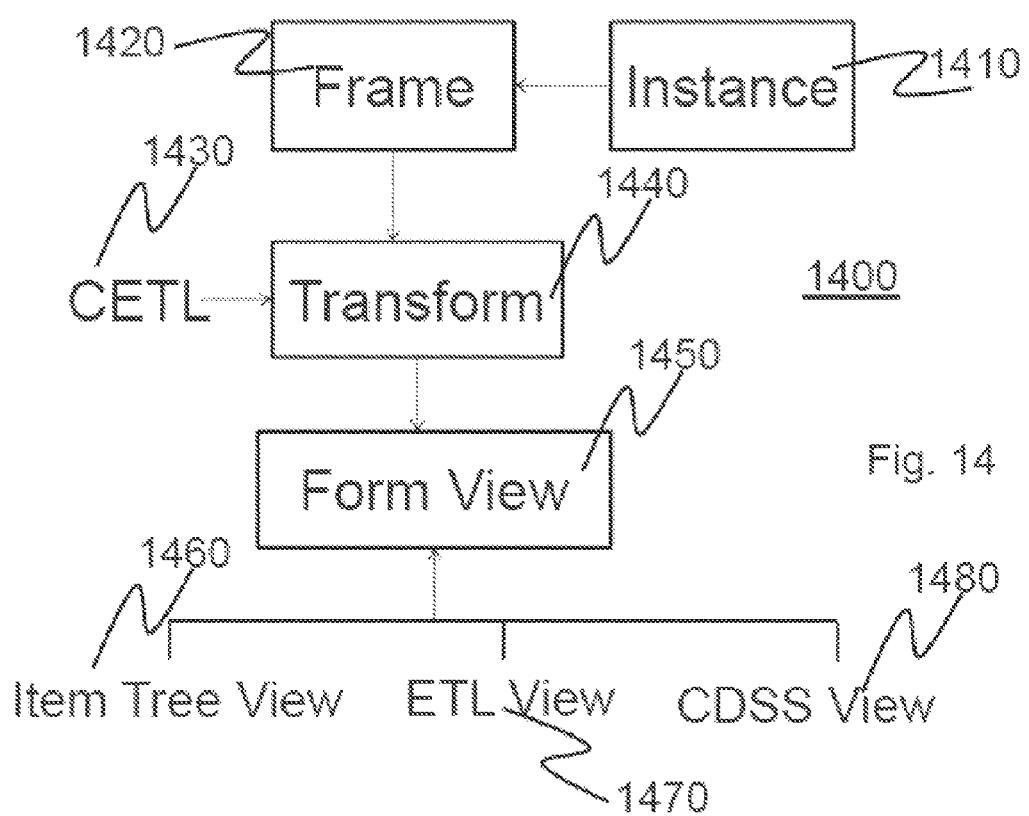
FIG. 14 illustrates an example system in which one or more instances are provided for a frame.

FIG. 14 illustrates an example system 1400 in which one or more instances 1410 are provided for a frame 1420. The frame 1420 is provided for a transform 1440 in conjunction with CETL 1430 to generate a form view 1450. As shown in the example of FIG. 14, one or more of an item tree view 1460, an ETL view 1470 and a clinical decision support system (CDSS) view 1480 are also used to generate the form view 1450.

Figure 15:
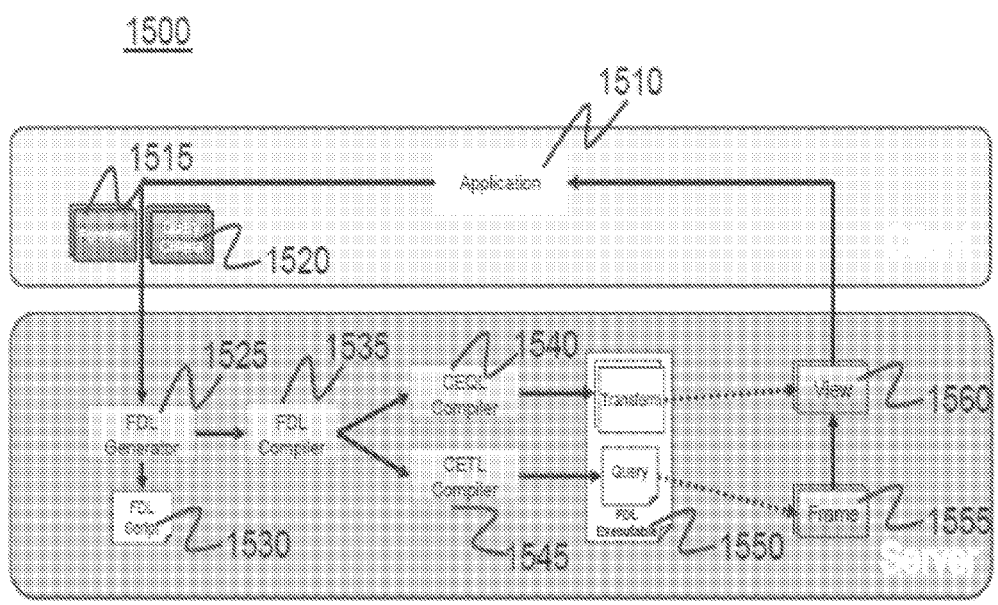
FIG. 15 depicts an example client-server system configuration to generate an application for execution via the client.

FIG. 15 depicts an example client-server system configuration 1500 to generate an application 1510 for execution via the client. As shown in the example of FIG. 15, query criteria 1515 and formlet(s) 1520 are provided to an FDL generator 1525, which produces an FDL script 1530 and provides information to an FDL compiler 1535 to generate FDL including a CEQL component and a CETL component. A CEQL compiler 1540 processes the CEQL component and a CETL compiler 1545 processes the CETL component to provide an FDL executable 1550 including both a query and a transform. The query provides data for one or more frames 1555 and the transform determines a view 1560 using the frame(s) data 1555 to provide the application 1510.

Figure 16:
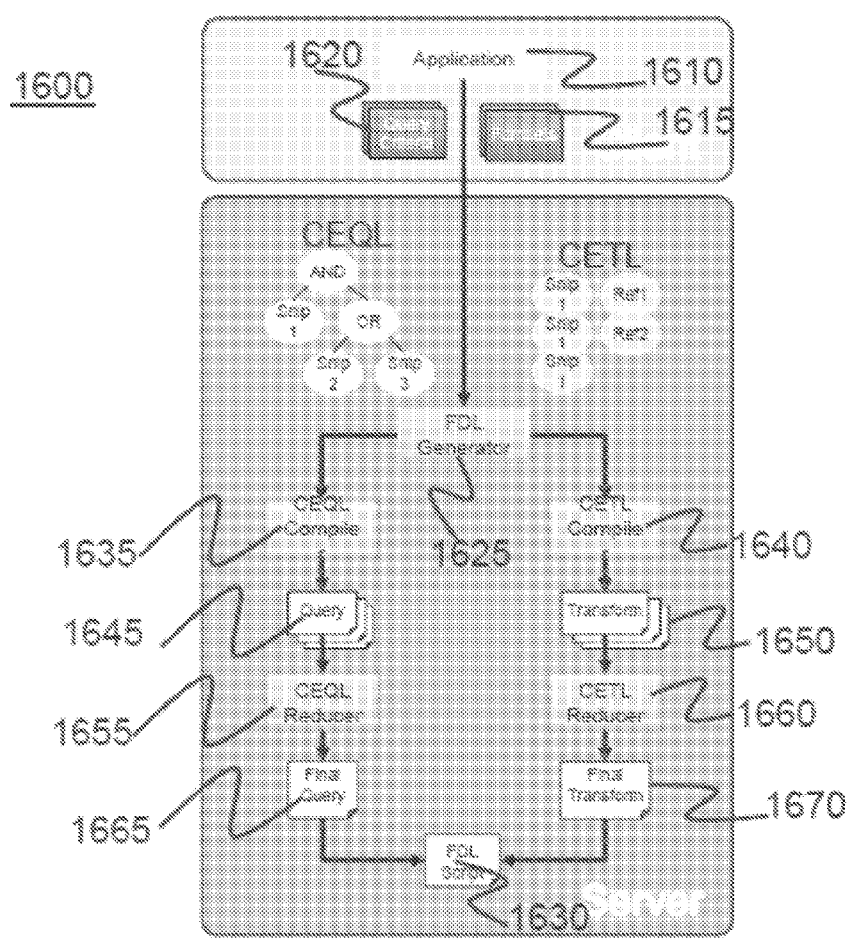
FIG. 16 illustrates an example client-server system configuration to generate an application for execution via the client.

FIG. 16 illustrates an example client-server system configuration 1600 to generate an application 1610 for execution via the client. As shown in the example of FIG. 16, query criteria 1615 and formlet(s) 1620 are provided to a server including an FDL generator 1625 employing CEQL and CETL to generate an FDL script 1630 related to the application 1610. As shown in FIG. 16, the FDL generator 1625 provides information to a CEQL compiler 1635 and a CETL compiler 1640 to generate a query 1645 and a transform 1650, respectively. The query 1645 is provided to a CEQL reducer 1655 to reduce a plurality of query results into a single output, resulting in a final query 1665. The transform 1650 is provided to a CETL reducer 1660 to reduce a plurality of transform components, resulting in a final transform 1670. The final query 1665 and final transform 1670 combine to produce the FDL script 1630.

VII. Enabling and Improving Clinical User Experience Via Formlets

Clinical information systems provide a large amount of data in one or more databases and/or other data stores, often in a particular defined form. For users and end-user systems, however, there are widely varying data display needs, requirements, preferences, etc. Clinicians may need or desire to view data stored in one or more databases in a specific, meaningful way, depending on application. Clinician and/or application requirements and/or preferences evolve, and certain examples enable clinicians and supporting systems to react quickly by providing new display forms for the data. Healthcare-related applications take a long time to develop and stabilize and are typically disparate in ways in which the applications present data. Certain examples provide components that can be reused and configured at runtime to form one or more applications and/or data views. Rather than displaying data in fragmented and/or out of context views, a patient's data can be woven together in a cohesive story via an integrated user interface using formlets, for example.

Formlets provide context-aware levels of detail to a clinical user and serve as a core building block to flexible, configurable clinical applications. Formlets provide a link of rich capability between a clinical database and clinical users. For example, formlets provide an ability to combine data fields from multiple entities in a clinical database. Formlets provide flexible ways to transform the data, including sorting, statistics, hierarchical rollups, formatting, etc. Formlets provide a description of how to display transformed data via a user interface, for example. Increasingly detailed views of the data can be provided via the user interface driven by the formlet, for example.

Using formlets to create an application, a large amount of information is presented in a consumable way that easily integrates into a user's workflow and mental model. A formlet-based interface allows the clinician to quickly make critical decisions, supports critical decision support and care collaboration, etc.

In certain examples, formlets are a core building block for an array of clinical application capabilities, including to tell a patient's story, allow surfacing of clinical data at varying levels of detail, provide clinicians with a runtime ability to author new data displays, provide clinicians with a runtime ability to configure existing applications, provide clinicians with common components that they can view in varying contexts, etc.

Using formlets, data can be tied together in an integrated, meaningful way. For example, a formlet can tie data together to tell a patient's story while highlighting critical details. A formlet can tie data together to summarize clinical unit operations, for example. A formlet can tie data together to summarize a unit acuity level (e.g., accumulation of patient acuities to determine overall score for a unit, etc.), for example. A formlet can tie data together to allow analytics for higher-level views of the data, for example. In certain examples, a formlet can take raw data and apply clinical knowledge to present the data in a way that is meaningful to a clinician.

For example, formlets can be provided to facilitate viewing of patient demographic information at a variety of levels of granularity. At the highest level, a grid cell shows the patient name only. This cell contains a formlet that draws the three patient name parts (last, first and middle name) from a clinical database and surfaces the patient name parts in the cell. At the next level, a hover shows the patient name, unit number, and age. The hover contains a formlet that is configured to manage this deeper level of detail (e.g., to query and surface the name, number and age components). At the next, inspector level, the inspector contains a formlet that queries and surfaces a full complement of demographic information. At the final depth of the example (e.g., the Single Patient View), multiple configurable formlets query and surface a wealth of available information about the patient (including demographics, labs, tasks, etc.).

Formlets can also show graphs, which support graph display in cells, hovers, inspectors, and the single patient view, for example.

In certain examples, a formlet includes a query, a transform, a data template, and binding instructions. A query specifies data to retrieve from a database, such as a clinical data repository, clinical data warehouse, electronic medical record, etc. The query can specify fields from varying clinical entities (e.g., patient age, visit number, laboratory results, etc).

A transform specifies how to transform the data into a form that is meaningful to a clinical user (e.g., a requesting clinical user, a user type, a user role, a user at a particular facility, etc). An example transform includes extracting values from the last twenty-four (24) hours of glucose lab results and placing the results in an array that can be included in a chart. An example transform includes determining if a lab panel is abnormal by checking to see if any of the panel's child observations are abnormal. An example transform includes sorting lab values by a time at which the results were returned from the laboratory. In certain examples, a transform results in a ViewModel object, which can be consumed by a View.

A data template specifies visual components (e.g., labels, graphs, text boxes, layout, etc.) for the formlet. For example, the data template can define and relation visual components forming part of the view. A data template can also provide visual styling instructions for the visual components of the formlet. A visual style defines an appearance and/or arrangement of components on the interface or view (e.g., color, background, text attribute(s), positioning, etc.).

Binding instructions specify how the ViewModel is to be bound to the data template. For example, formlets can provide unique, reusable components that can be placed in an application in a plurality of places. For example, a user interface can provide a view based on one or more formlets and associated data and/or functionality. A hover box, whose content is managed by a formlet, can also be provided.

Using the query, transform, data template, and binding instructions, formlets apply clinical knowledge to clinical data, so the clinical data becomes more meaningful to a reviewing/applying clinician. Runtime authoring and configurability empowers clinicians and enterprises to create applications that fulfill their needs and/or wants without requiring a round-trip to engineering resources. Formlets allow sharing of clinical knowledge between and within institutions. Using formlets, enterprises can manage certain populations of patients, for example. A combination of formlets displaying population data allows one or more populations of patients to be managed, for example. A cohesive, clear patient story provided via a formlet leads to lower readmissions and better patient outcomes. Data organized and presented via a formlet helps allow hospitals and clinics to run more smoothly based at least in part on up-to-date visibility into operations, data, a correlations.

Generation of formlets to apply a query, a transform, a data template, and binding instructions to data facilitates reuse of code resources and reuse of testing resources, for example. For example, one well-tested formlet can be incorporated into multiple applications. Using runtime creation, rather than development-time or compile-time creation, data can be aggregated, transformed, and visually presented without installation of software components and/or extensive manual coding by a custom developer. Using formlets, an organization can provide customers with quicker turnaround time, traditional and/or custom user controls, design surface with predefined visual elements, etc. Formlets provide users with controls and a well regulated mechanism to transform database queries into a defined form and visual presentation.

Certain examples provide one or more formlets organizing clinical data, rules and associations to tell a patient's story. The formlet leverages one or DCMs/CEMs to provide a template and build the form automatically. By providing an integrated story for a patient and clinician/group of clinicians, a more intelligent viewing of data can be facilitated for particular circumstances beyond a dashboard summary. The formlet ties together data and publishes the combined data for user review and/or interaction along with a surfacing of associated actions. In certain examples, a formlet can be dynamically configured at run-time. In certain examples, formlets can have relationships and communicate with other formlets.

Using one or more views defined according to one or more formlets, a user story and resulting strategy for diagnosis and/or treatment of one or more patients can be defined.

Review of and interaction with data can be facilitated for an individual clinician and/or an entire team involved with a patient and/or group of patients, for example. In certain examples, transition of care can be facilitated via a formlet-defined interface. For example, handoff of a patient within an organization, between organizations, etc., can be facilitated. In certain examples, different clinicians can log in and review patient information at the same time (e.g., simultaneously or nearly simultaneously, etc.). Thus, an originating department and a transfer department can both review patient data via a formlet.

In certain examples, a multi-patient view can be formulated using one or more formlets to arrange patient data and associated functionality, rules, relationships, etc. Via the MPV, a user can select (e.g., click on, hover over, etc.) a patient to retrieve a patient story in an Inspector. Via the inspector, critical elements for a unit can be displayed along with referring/consulting physicians, labs pending, etc. Presentation of information can be differentiated based on user (e.g., a physician does not want to see nurse notes, a nurse sees both types, etc.), for example. By selecting handoff in the inspector, a user can see notes from other clinicians, reminders, etc. Two doctors can both conduct a real-time (or substantially real-time) review and co-document on the same patient at the same time, facilitating simultaneous (or substantially simultaneous) access into the same record by different users. Formlets provide a framework to govern what a user sees and how the user sees it.

Formlets can provide a motif for using cells, hovers, inspectors and single patient view to organize and surface patient data and associated functionality. A common chassis allows applications to build on common mechanisms to reveal detail to the user. These mechanisms are enabled by a common software development kit, which allows for rapid application development, for example. Formlets facilitate a common look and feel and provide guidance to application developers regarding visual metaphors to use in configuring and/or otherwise customizing their interfaces using the formlets. Further, the underlying technology of formlets provides varying levels of detail to allow for reuse, since more than one application can use the same formlet.

In certain examples, formlets facilitate taking of data from a plurality of source systems and displaying the data in one location. Formlets support quick clinical decisions by presenting large amounts of data that matches the users' workflow, for example.

For example, a multi-view helps a user manage a clinical unit (e.g., provides a list of a doctor's patients, etc.). A single view tells a patient's story and goes into one or more source documents to diagnose and treat a patient. Integrating information from an electronic health record, medical monitoring device(s), other systems, etc., helps to facilitate diagnosis and/or treatment, for example. A user can access information and execute functionality to diagnose and treat a patient from one location (e.g., one view).

Reminders can be provided to communicate from physician to physician (e.g., like a sticky note on a physical file, a to do list, etc.). A user can be associated with a reminder (e.g., name, date, time, etc.). A reminder is stored and can be shared but is typically not saved in a patient's legal record.

If a patient is transferred between departments, the view can switch from a unit view to a patient view, for example. A transferred patient can automatically appear on a doctor's list, for example. A patient can be selected from a multi-patient view for a single patient view, for example. Selecting an item displayed via the view can take a user to a source system to interact with the data (e.g. so a user can see an EKG done, can enter an order, etc.). An action can be done in the source system and then revert back to a single/multi-patient view. Results can be populated in this view, for example.

In certain examples, updating an item in a formlet results in an update of the item in a corresponding database and/or other data store. For example, the item returns in an update or refresh from a database to the same and/or other formlet. In certain examples, formlets can talk to each other and can be associated in one or more relationships. In certain examples, a change in data coming in from a back-end system (e.g., a new vital) appears in the view. Vital signs are continuous, so the view can facilitate real-time, continuous gathering and display of vitals (or at least near real-time, near continuous gathering and display of vitals, etc.).

Using a formlet-generated view, vitals can be compared to medications for a patient and/or group of patients. A user can selected (e.g., click on, hover over, etc.) to view date, time, source, route, etc., for medication at a point of administration. A view can provide information regarding multiple points of administration (e.g., morning, afternoon, etc.) and can see impact of medication(s) on vital(s) according to a formlet specifying one or more models for data, rules, functions, etc. Medication such as insulin can be administered on a sliding scale for disease management, etc., and can be represented in a view via a formlet for user review and interaction.

In an example, a clinician reviews a patient suffering from congestive heart failure, and the patient view formlet provides a guideline for two medications. The user can document, via the interface, why the user did or did not follow the guideline. The patient view formlet provides daily weight and trending, ejection fraction displayed, etc. A user can tailor the view to add his or her own protocol with information in a single interface. In certain examples, a trigger for retrieval and/or organization of patient data is a principle diagnosis on that patient, not just admission of the patient.

Figure 17:
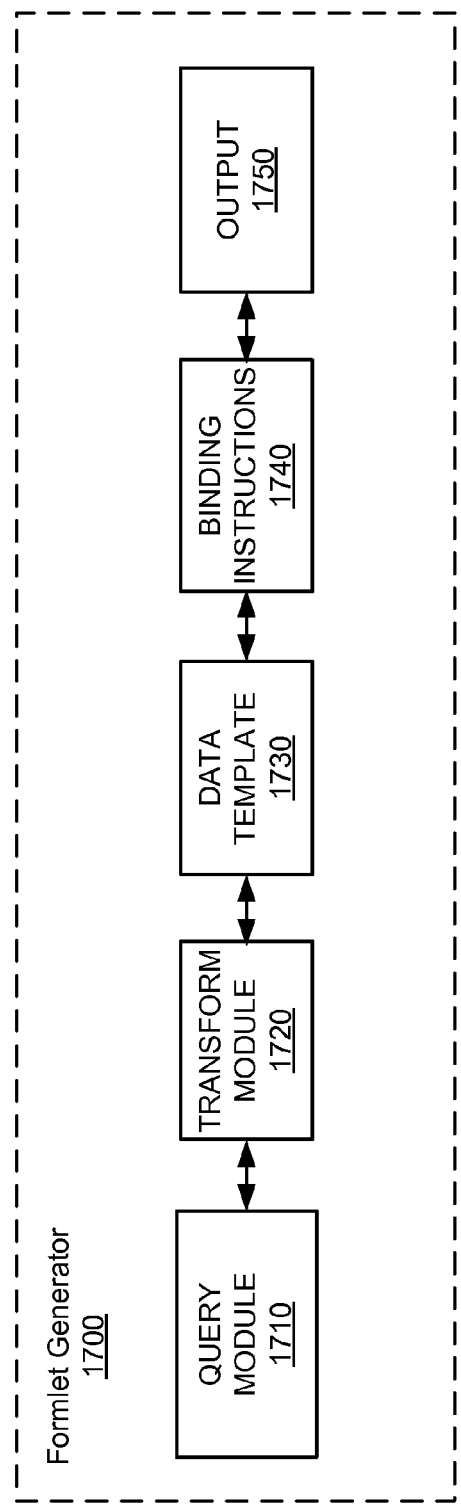
FIG. 17 illustrates an example formlet generation system.

FIG. 17 illustrates an example formlet generation system 1700. The system 1700 includes a query module 1710, a transform module 1720, a data template 1730, binding instructions 1740, and an output 1750. The query module 1710 generates a query. The query specifies the data to retrieve from a clinical data source, such as a database, data repository, data archive, etc. The query can specify one or more data fields from varying clinical entities (e.g., patient age, visit number, laboratory results, etc.), for example. The query module 1710 facilitates execution of the query to retrieve data.

The transform module 1720 specifies how to transform the retrieved data into a form that is meaningful to a clinical user (e.g., a requesting clinical user, etc.). For example, a transform can specify that the system 1700 is to extract values from the last 24 hours of glucose lab results and place them in an array that can be formatted and displayed in a chart. An example transform can determine if a lab panel is abnormal by checking to see if any of the panel's child observations are abnormal. An example transform can specify to sort lab values by the time the lab values are returned from the laboratory. The transform results in a ViewModel object, which can be consumed by a View and/or other graphical user interface, for example.

The data template 1730 specifies visual components (e.g., labels, graphs, text boxes, layout, etc.) for the formlet. The data template 1730 also provides visual styling instructions, for example.

The binding instructions 1740 specify how the ViewModel is to be bound to the data template 1730. Formlets are unique, reusable components that can be placed in an application in a number of places, for example, and binding instructions 1740 can help facilitate their use in a viewer and/or other interface. The output 1750 provides a resulting view and/or other form (let) based on the retrieved, transformed data organized according to template and binding, for example.

A user can use the formlet generation system 1700 to generate, customize, and/or configure a formlet for user in an interface and/or other application, for example. Formlets provide a link to rich capability between a clinical database and clinical users, for example. Formlets provide an ability to combine data fields from multiple entities in the database, as well as flexibility to transform that data, including sorting, statistics, hierarchical rollups, formatting, etc. Formlets provide a description of how to display the transformed data on the user interface. Via the formlet generation system 1700, formlets can provide core building block for a rich array of clinical application capabilities.

Figure 18:
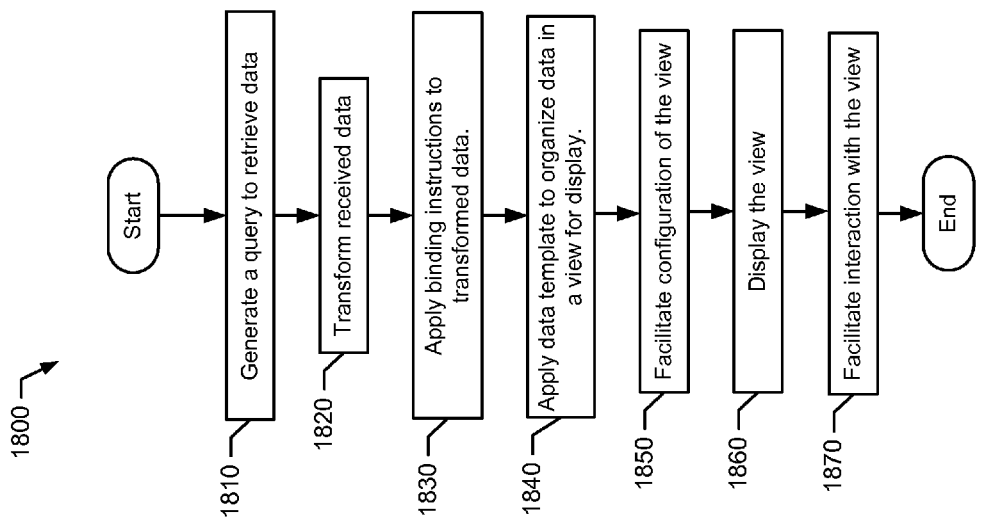
FIG. 18 illustrates a flow diagram of an example method to generate a formlet to display and facilitate interaction with clinical data.

FIG. 18 illustrates a flow diagram of a method 1800 to generate a formlet to display and facilitate interaction with clinical data. At block 1810, a query is generated to retrieve data. The query specifies the data to retrieve from a clinical data source, such as a database, data repository, data archive, etc. The query can specify one or more data fields from varying clinical entities (e.g., patient age, visit number, laboratory results, etc.), for example.

At block 1820, the retrieved data is transformed into a form that is meaningful to a clinical user (e.g., a requesting clinical user, etc.). For example, a transform can specify that values from a certain time frame and/or other criterion(-ia) are to be extracted, sorted, evaluated, and/or placed in a data structure (e.g., an array, etc.) to be formatted and displayed for user review. A transform can include applying analytics to the queried data. In certain examples, the transform results in a ViewModel object, which can be consumed by a View and/or other graphical user interface, for example. In certain examples one or more transforms result in one or more objects to be used to provide a View to a user.

At block 1830, binding instructions are applied to specify how the transformed data (e.g., the ViewModel) is to be bound to the data template. Formlets are unique, reusable components that can be placed in an application in a number of places, for example, and binding instructions can help facilitate their use in a viewer and/or other interface.

At block 1840, a data template is applied to organize the transformed data in a view for display. For example, the data template specifies visual components (e.g., labels, graphs, text boxes, layout, etc.) for the formlet view. The data template can also provide visual styling instructions, for example.

At block 1850, configuration of the view is facilitated. A user can author new data displays, configure existing applications, view and arrange preconfigured components in varying contexts, etc. Configuration can be facilitated at runtime, for example.

At block 1860, the view is displayed. For example, the user can view the formlet as a standalone interface, as part of a larger interface (such as an MPV, etc.), on a mobile device, on a personal computer, etc. One or more formlets, frameset, rules, models, etc., can be used to facilitate display of the view. Thus, clinical knowledge and/or other relationships, rules, constraints, etc., are applied to present the data in a way that is meaningful to the clinician.

At block 1870, interaction with the view is facilitated. For example, a user can surface varying levels of clinical detail for a patient and/or patient population via the formlet view to tell the patient's story and assist in diagnosis and/or treatment. Data is tied together via the interface to tell a patient's story while highlighting critical details for the patient. "Critical" details may vary based on reviewing user, unit, urgency, and/or other conditional variable, for example. Information such as clinical unit operations, unit acuity level, etc., can be summarized for user review and/or other interaction via the view, for example.

Figure 19:
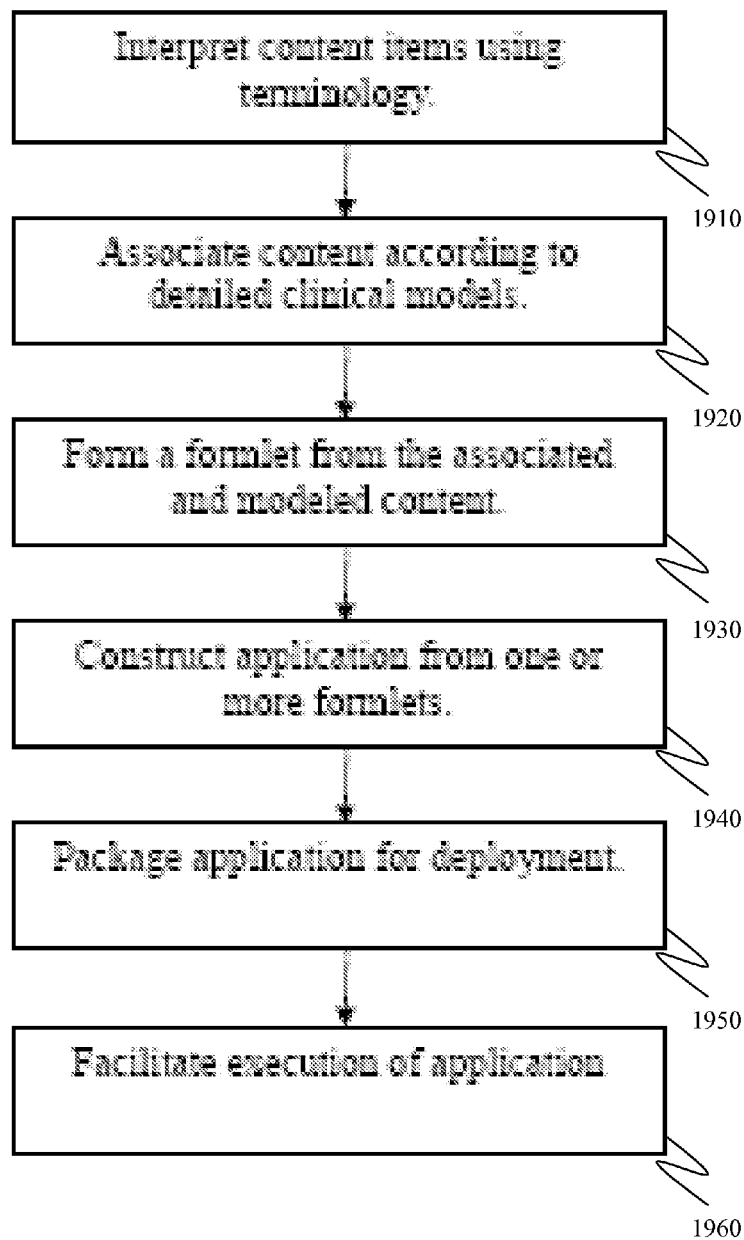
FIG. 19 illustrates a flow diagram of an example method of heuristic content resolution in an extensible content management system.

FIG. 19 illustrates a flow diagram for an example method 1900 of heuristic content resolution in an extensible content management system. For example, a particular content item, such as content item 510 shown in FIG. 5, may have a plurality of context variants which may in turn have a plurality of context variants. A heuristic and/or other algorithm can be applied to identify an appropriate (e.g., a most appropriate) context variant for a particular content item based on one or more criterion (e.g., a user's current context). This can be referred to as context resolution. Context resolution involves conditioning a selection, composition, and/or behavior of a content item based on a specified value, such as a context of the user.

Context resolution can occur at three levels, for example: selection of a content item, selection of a content frame, and translation of a content item. Selection of one or more content items on which a content item being deployed is dependent can occur based on context, for example. Selection of a content frame based on context can occur when the content frame is retrieved by an application. Translation of a content item based on context can occur when loading or retrieving a content frame.

Multiple variants of a content item can be resolved based on who, what, or where the content consumer is, for example. This allows users to create, specialize, and/or customize their own content on top of default or vendor-released content (e.g., shareable and interoperable content). This allows for a single content type to vary by properties associated with the content consumer without having to customize every application that consumes a particular content item to be aware of the appropriate rules to vary the display of the content.

In clinical applications, content can be displayed in different ways based on a context of application use. For example, a role of a clinician may impact what clinical information the user wants to see and how the user wants to see it. A location of a user can also impact the type of information that is desired to be displayed based on clinical need and preference, for example. There is also a need to display clinical information in multiple languages, especially for patients.

At block 1910, a content item is identified. The content item can be identified in conjunction with a formlet combining a plurality of content items according to one or more clinical element models, for example. The formlet may be part of a form to provide information and functionality to a user according to one or more clinical element models, for example. Identification and context resolution can occur at runtime, at packaging, etc.

At block 1920, available context variants for the content item are identified. For example, a content item can be stored in a clinical repository along with a plurality of context variants and an indication of the available context variants for that content item. Context variants can be identified based on an input context value or values (e.g., metadata associated with the content indicating user, role, location, namespace, department, etc.) provided at runtime, packaging time, etc., for example.

At block 1930, conflicting context variants are rejected. For example, if an input context indicates a language of "English" and a role of "nurse", then conflicting variants from the pool of variants including "French", "doctor", etc., are rejected or eliminated from consideration.

At block 1940, more specific context variants are rejected. For example, for an input context of English nurse (e.g., "en/nurse"), context variants that provide additional detail/variation, such as Labor and Delivery (e.g., LDS), Labor and Delivery Nurse, etc., are eliminated or removed from consideration.

At block 1950, a most specific variant of the remaining context variants for that content item, is selected. For example, continuing the English nurse context input example, remaining variants English (e.g., "en") and English nurse (e.g., "en/nurse") are reviewed to select a most specific remaining variant. In this example, that context variant is Triage English nurse. That context variant is selected for use as the particular content item for the clinical application (e.g., a formlet forming part of a form).

Resolution of context by an application allows appropriate information to be displayed based on who, what, and/or where the user of the application is. This ability enables streamlined workflows and targeted documentation for clinical use. This also gives flexibility to customize content for specific use(s). Thus, context selection or resolution utilizes a heuristic to resolve ambiguity or conflict among available context variants (e.g., weighting or priority schemes, default rules, etc.). Changing/adding a context variant, changing weight of a context attribute, etc., can change context resolution on another content item, for example.

VIII. Context Sensitive Level of Detail

Certain examples provide a context sensitive level of detail via one or more formlets. A user can view clinically relevant data/information for a single patient within a context of a population. Clinically relevant data and/or other information can be viewed at various levels of detail including, for example, a unit/list view, single patient view, hover, inspector, etc. Various levels of detailed and trend views offer a comprehensive and comparative advantage to aid users in their clinical decision support, analytics, and plan of care, for example.

Figure 20:
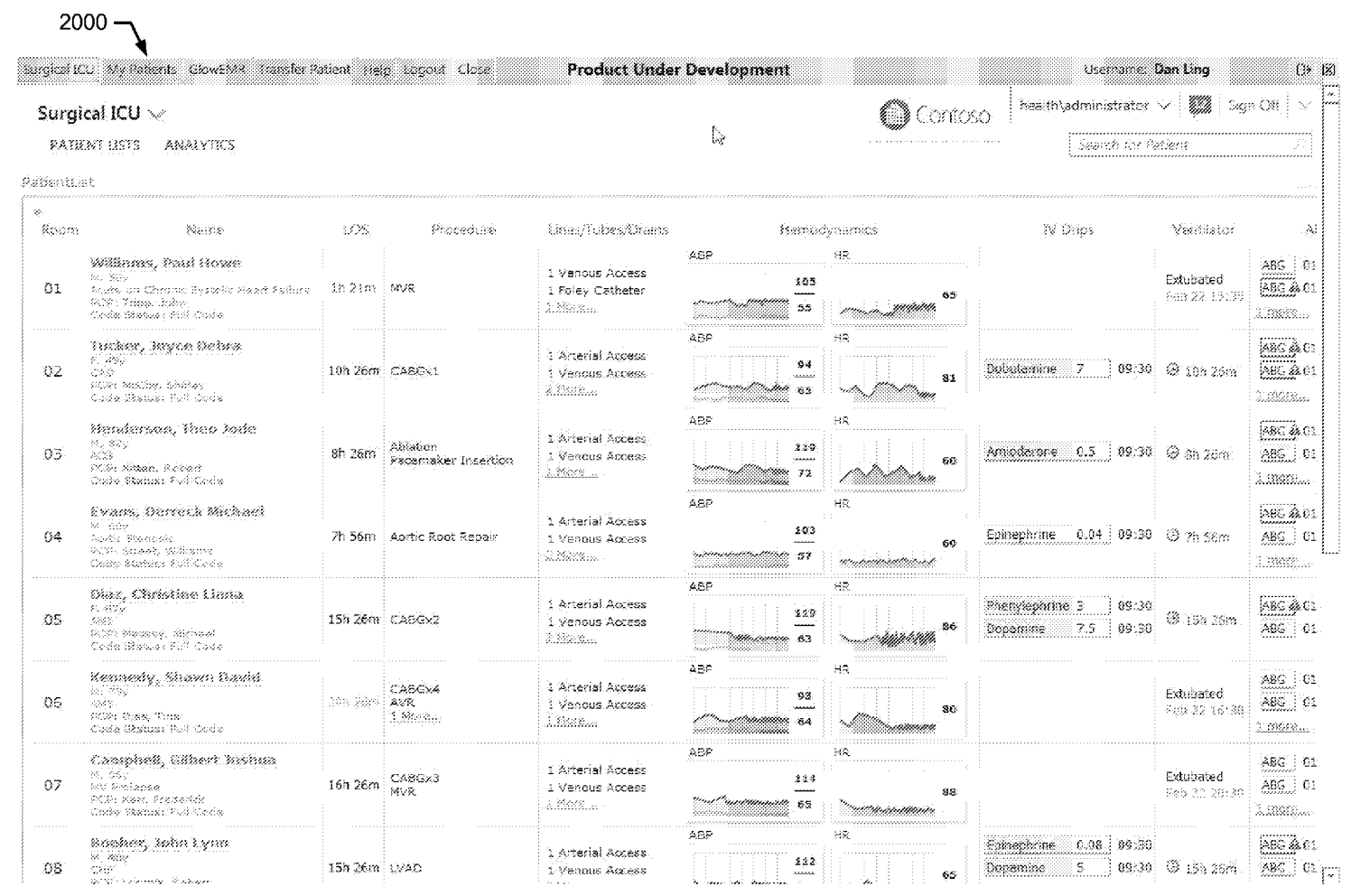
Figure 21:
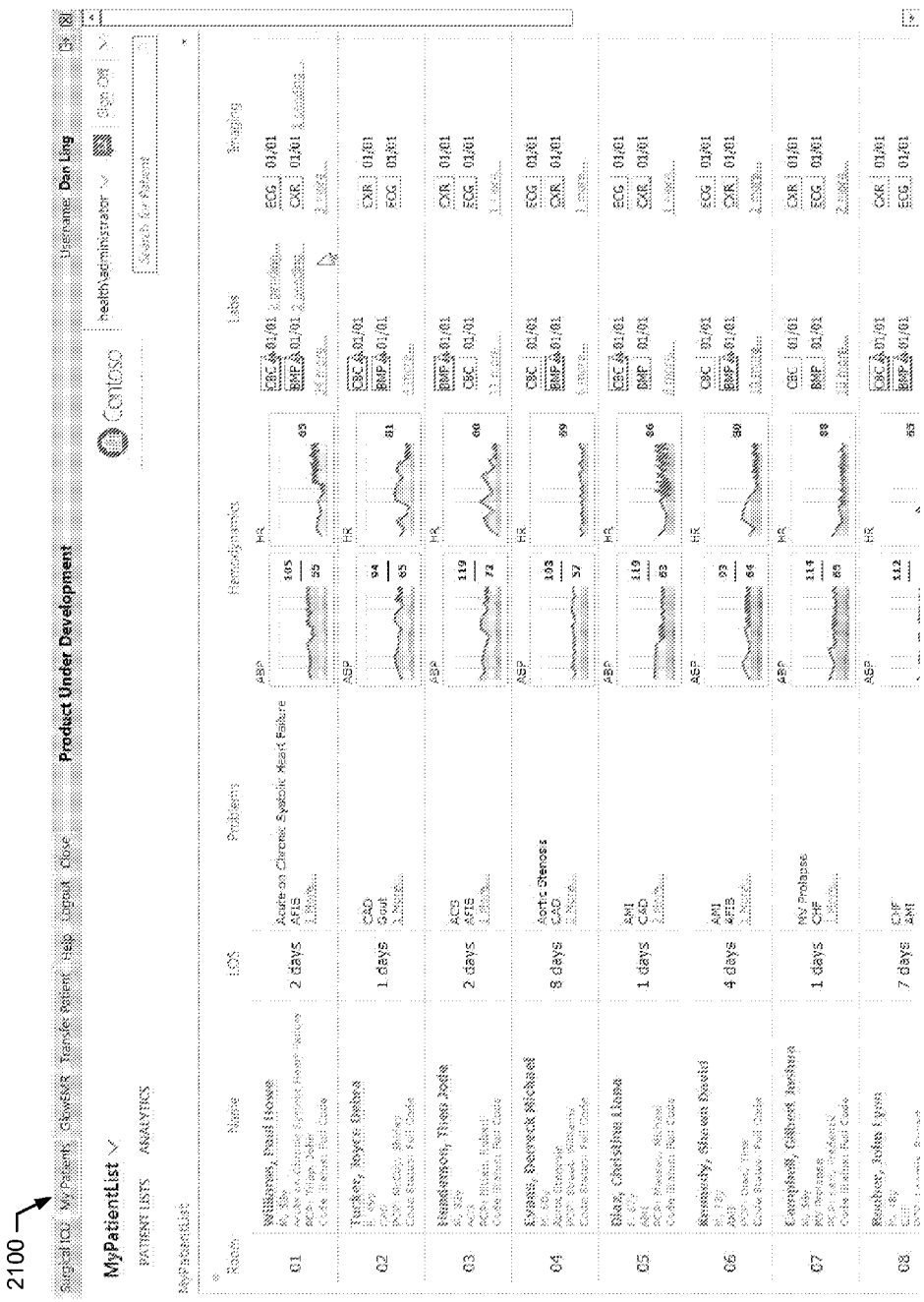

FIG. 20 illustrates an example multi-patient view interface 2000 formed from a plurality of formlets including underlying frames and clinical models. A user can access the surfacing of more detailed information from the multi-patient view, as well as from a list view 2100 illustrated in the example of FIG. 21. The user can configure the display of patients in all list views and associated data and/or other information via one or more configurable formlets, for example. Each component (e.g., a cell, section, etc.) of the example views 2000, 2100 is generated using a model associating content which organizes data and functionality to form a portion or cell of the interface (e.g., a formlet). The cells can be in turn associated and additional views may be generated.

Figure 22:
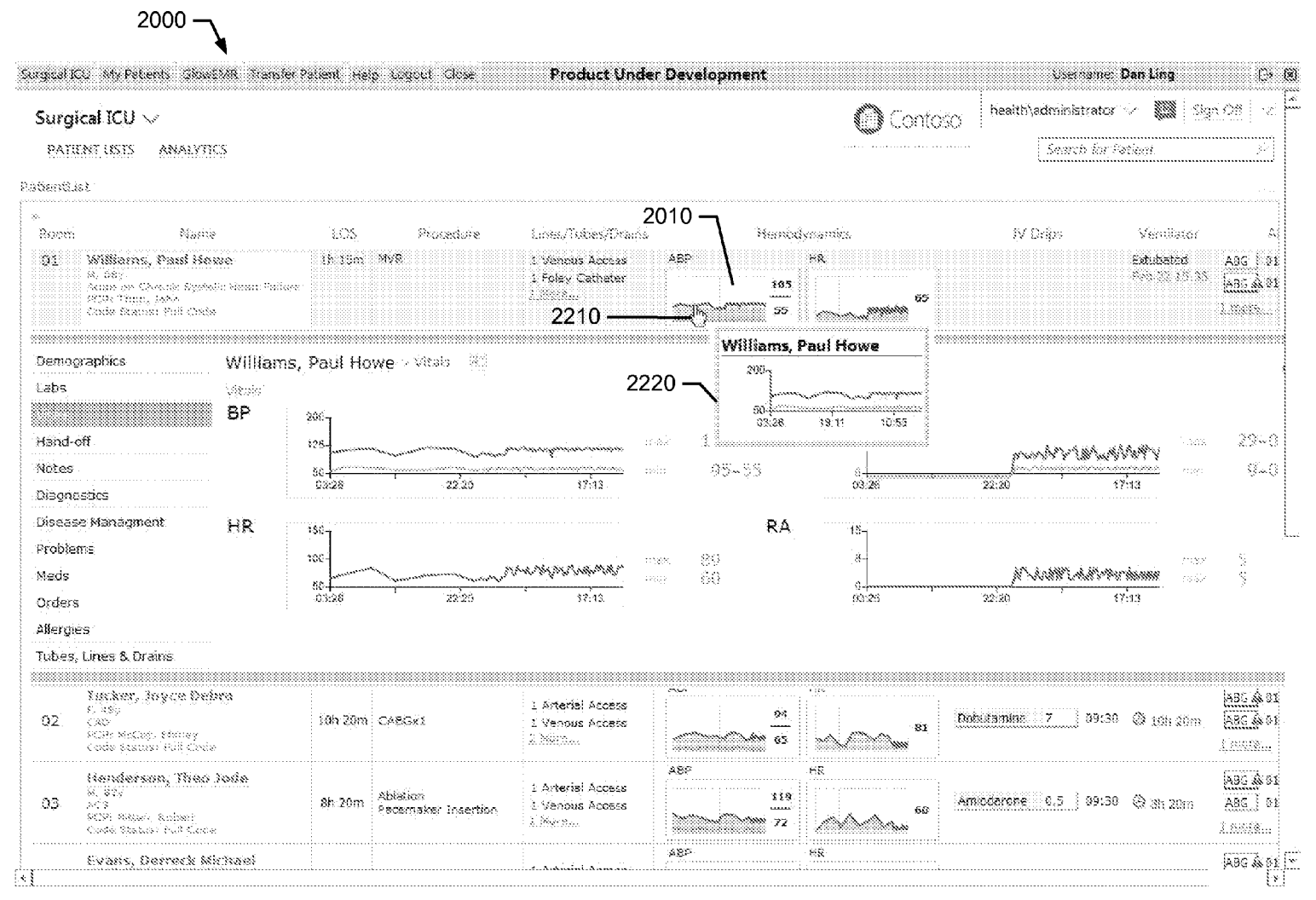
Figure 23:
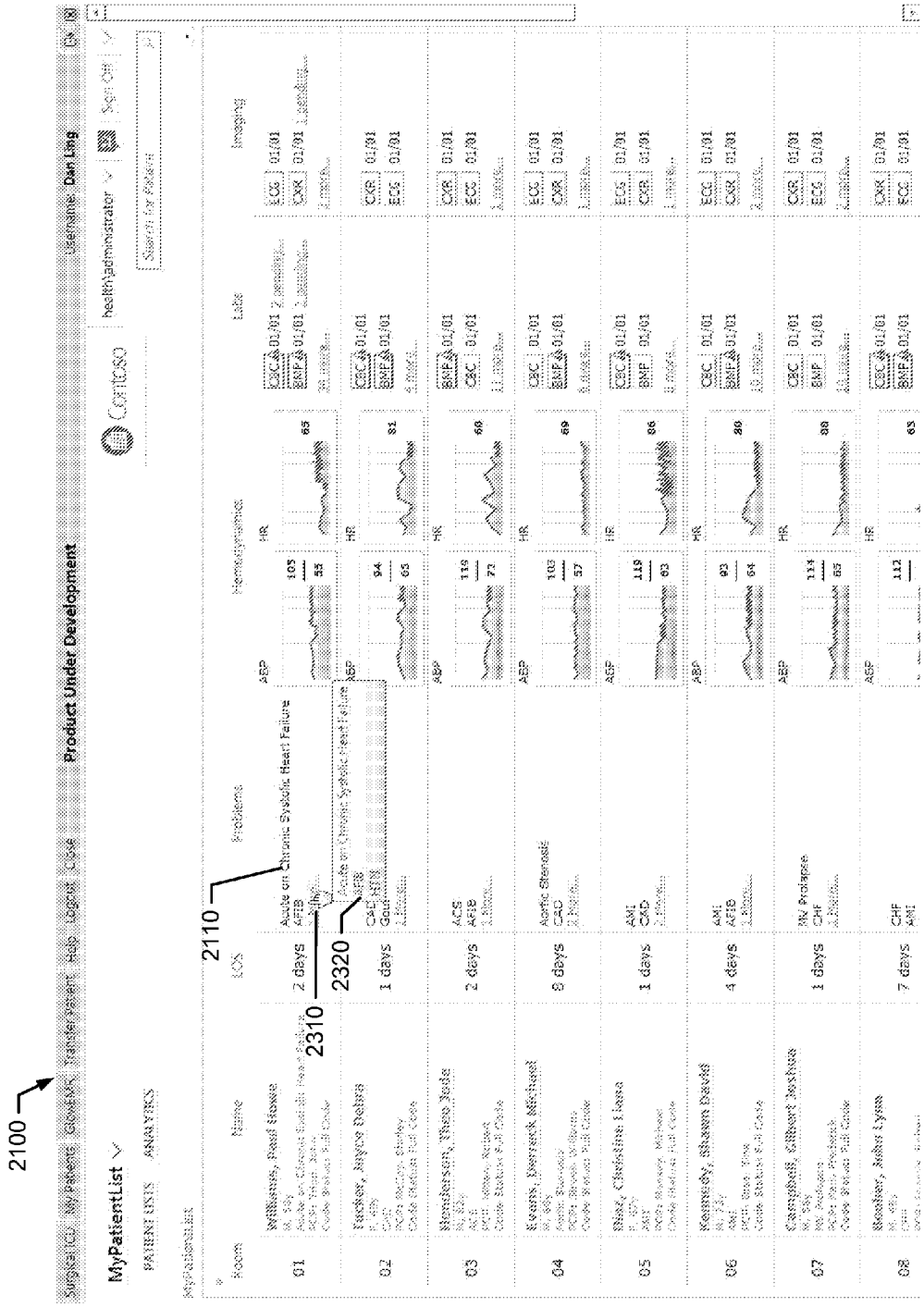

As illustrated in FIGS. 22 and 23, a first degree of additional detail can be accessed by hovering over a portion of the high-level interface view 2000, 2100. By hovering over a cell 2010, 2110 in the high-level view 2000, 2100, additional detail can be viewed and/or otherwise made available for user interaction.

As illustrated in FIG. 22, for example, positioning a cursor 2210 over the cell 2010, causes a hover view 2220 to be displayed. The hover view 2220 provides additional detail beyond that viewable in the 2010 in the high-level display 2000. Similarly, as illustrated in FIG. 23, for example, by user positioning of a cursor 2310 over the cell 2110, a hover view 2320 is displayed. The hover view 2320 provides additional detail beyond that viewable in the 2110 in the high-level display 2100.

Figure 24:
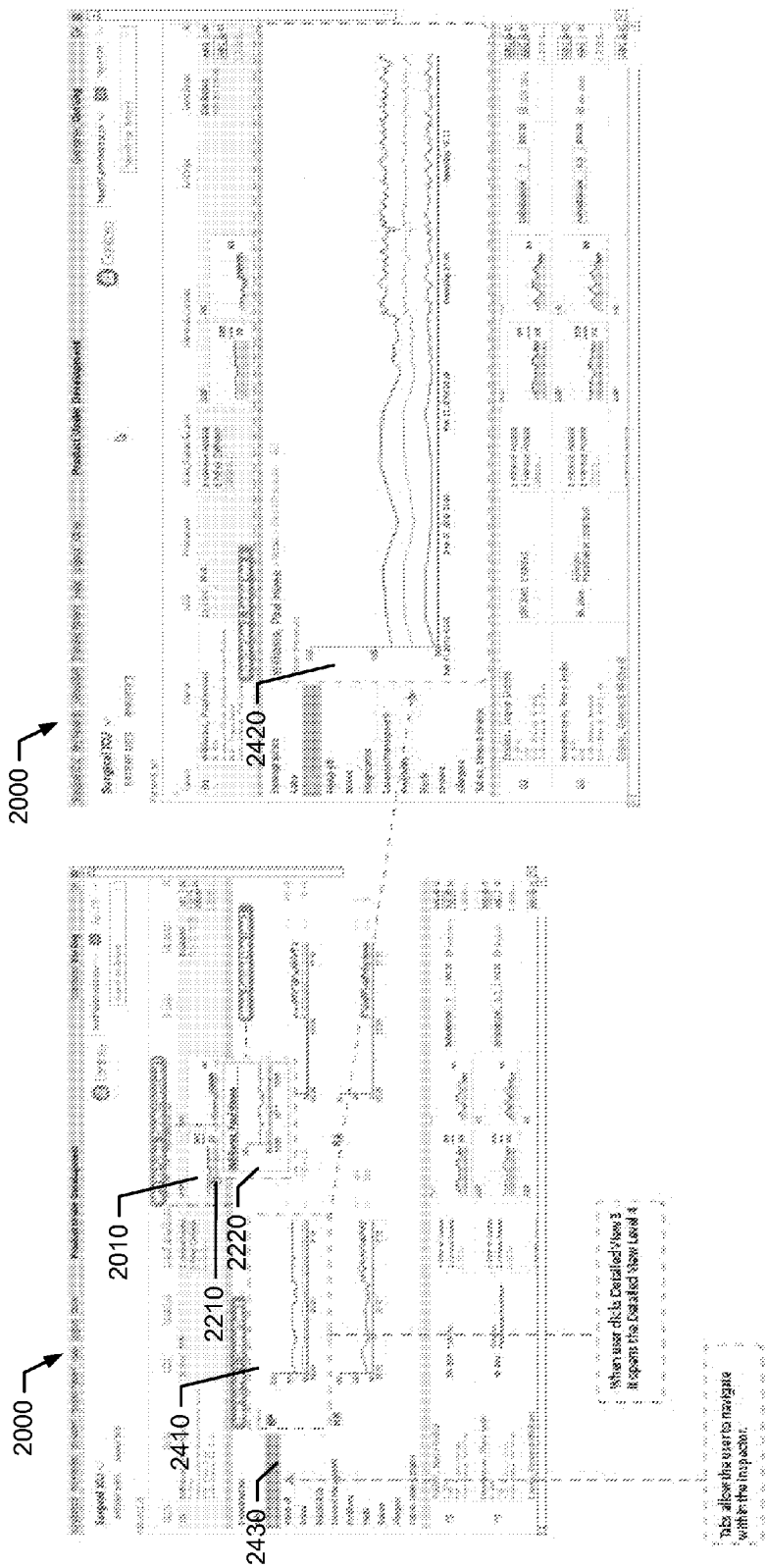

FIG. 24 illustrates an example inspector 2410 which provides a plurality of additional degrees of detail in the clinical data provided for view. As shown in the example of FIG. 24, the MPV 2000 provides an initial high-level view of data in a cell 2010. Upon hovering over and/or otherwise selecting the cell 2010 with a cursor 2210, a hover view 2220 is displayed to provide additional detail. The example MPV interface 2000 also includes an inspector view 2410 that can be activated by the user to provide further detail from the hover view 2220. The user can access the inspector 2410 by selecting the hover view 2220 and/or other interface 2000 option, for example.

When the user selects (e.g., clicks on, etc.) the first inspector detail view 2410, a second inspector detail view 2420 is opened. The second inspector detail view 2420 provides even more detail than the first inspector view 2410.

Further, one or more tabs 2420 provided with the interface 2000 allow the user to navigate within the inspector 2410, 2420 to view different types and/or degrees of information (e.g., demographics, labs, hand-off, notes, diagnostics, disease management, problems, medications, orders, allergies, tubes/lines/drains, etc.).

Figure 25:
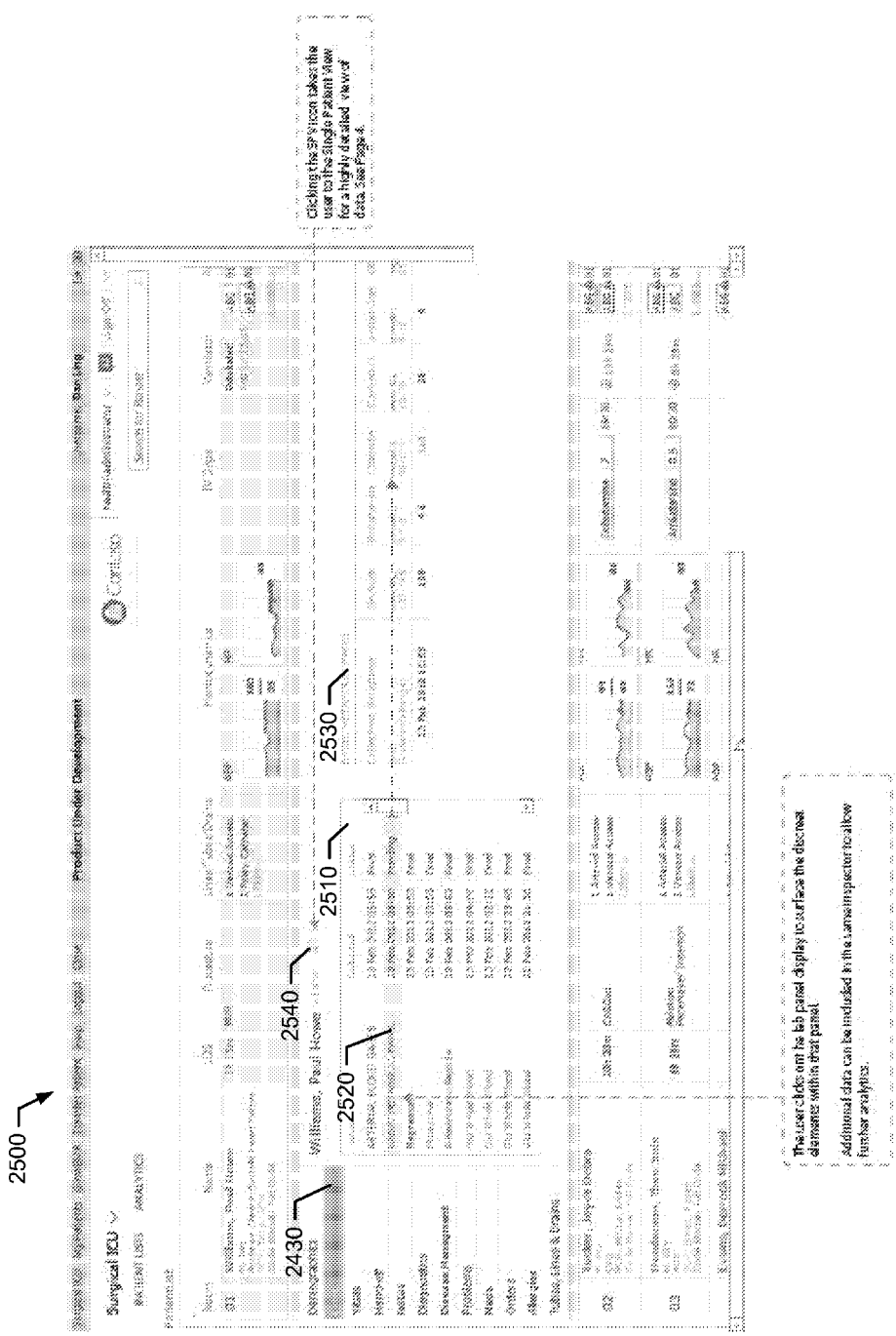

FIG. 25 illustrates the example MPV 2000 being navigated according to the inspector tabs 2430. Selecting a labs tab, for example, surfaces one or more discreet lab elements 2520 within the lab panel 2510. Selecting an element 2520 provides further detail 2530 regarding the selected element. Selecting a single patient view (SPV) icon 2540 takes the user to a single patient view 2600 (shown in FIG. 26) for a highly detailed view of data.

Figure 26:
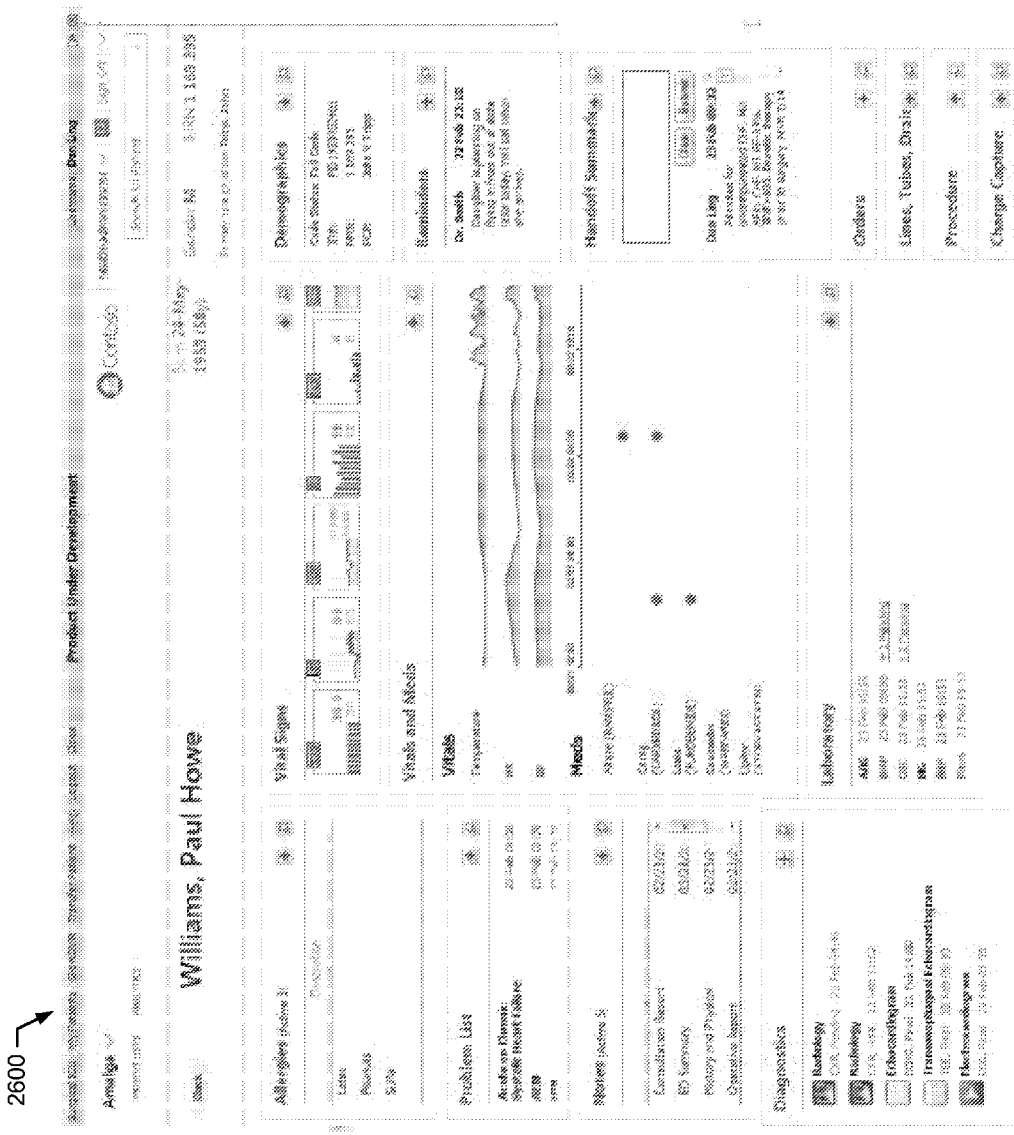

The example SPV 2600 depicted in FIG. 26 provides a comprehensive view of the data for the selected patient in one location. In certain examples, the user determines in both the MPV 2000 and the SPV 2600 what data and/or other information to display. The user configures the views 2000, 2100, 2600 via customizing/configuring one or more formlets, for example.

Figure 27:
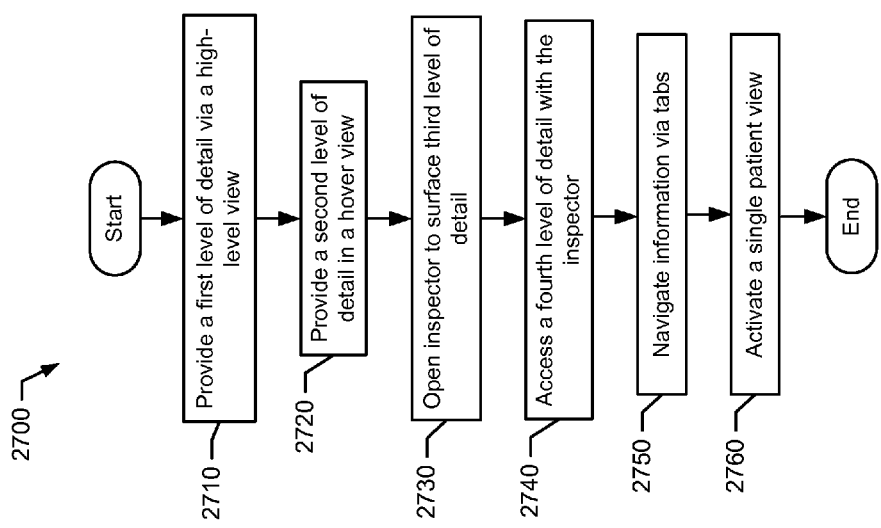
FIG. 27 illustrates a flow diagram for an example method to surface varying degrees of patient data via a formlet-based user interface.

FIG. 27 illustrates a flow diagram for an example method 2700 to surface varying degrees of patient data via a formlet-based user interface. At block 2710, a high-level view of one or more patients is provided with a first level of detail. For example, an MPV or patient list view is generated for a particular user from a plurality of formlets and displayed to that user for review and interaction.

At block 2720, hover view providing a second level of detail is generated in response to a hover of a cursor over a cell in the high-level view. For example, a user positions a cursor over a cell in the MPV, and a hover view providing a second level of detail for that cell is provided in conjunction with the MPV view.

At block 2730, an inspector is opened to access a third level of detail. For example, a user selects the hover view and/or otherwise activates the inspector to view a third level of detail regarding the selected item for the selected patient. At block 2740, a fourth level of detail is accessed within the inspector. For example, user selection of the opened inspector brings up a fourth level of detail regarding the selected content.

At block 2750, a variety of detailed information can be navigated via one or more tabs. For example, the inspector provides a plurality of tabs allowing the user to switch among levels of degree for a plurality of types of information for the patient.

At block 2760, a single patient view is activated. For example, a user can switch between an MPV and an SPV to provide a more comprehensive review of a patient's information.

Thus, certain examples facilitate drill-down and surfacing of a variety of clinical information based on formlets and user configuration. Certain examples provide a hover view to facilitate relationships between information as well as changes in scale and additional detail. Certain examples provide an inspector offering additional information and a collaboration tool for users. The inspector and hover views can be shown with respect to the rest of the high-level view, such as the MPV, and then allow the user to drill down for greater degree(s) of information and navigate among degrees and types of information, for example. Certain examples provide clinical analytics and decision support with respect to varying levels/degrees of clinical information. Certain examples allow visual surfacing of clinical protocols along with configurability, sorting, and other user options. Certain examples provide a workflow/methodology facilitating a multi-patient view, my patient view and single patient view for an organization or enterprise.

In certain examples, a hover provides one level of additional detail, and an inspector provides even more. A user can navigate from inspector to single patient view, for example. The hover can facilitate content-based provision of information, and different hovers can be provided. Varying degrees of correlation, scaling, and drill-down (e.g., multi-patient view, my patient list, single patient view, etc.) can be provided.

Figure 28:
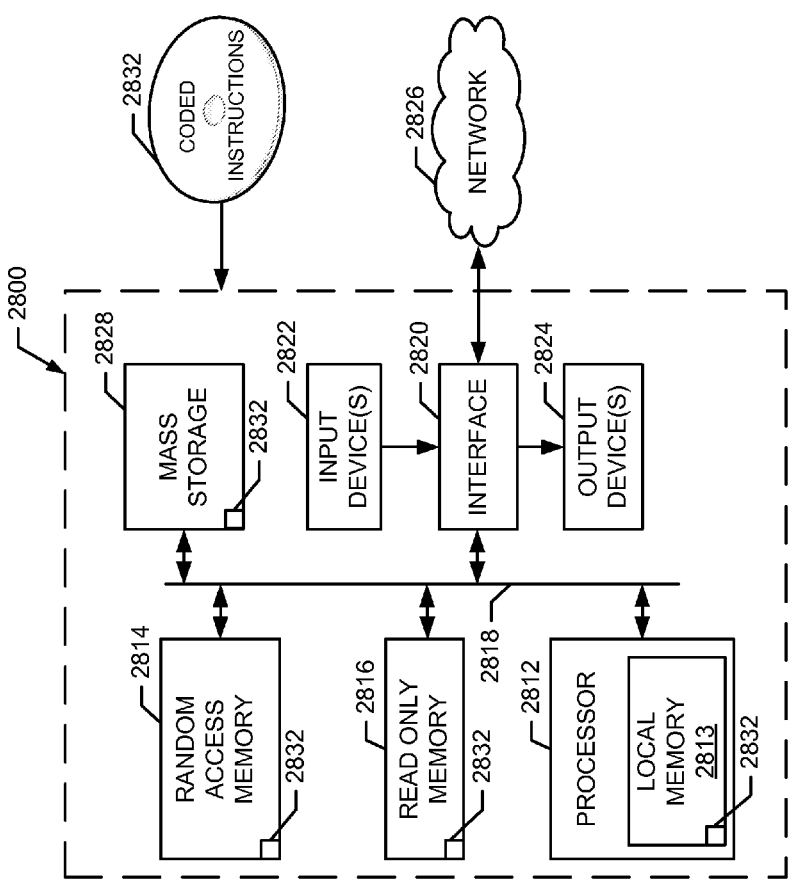
FIG. 28 is a block diagram of an example computer capable of executing instructions to implement the example systems and methods described above.

FIG. 28 is a block diagram of an example computer 2800 capable of executing instructions to implement the example systems and methods described above. The computer 2800 can be, for example, a server, a personal computer, a mobile phone (e.g., a cell phone), a personal digital assistant (PDA), an Internet appliance, a set top box, or any other type of computing device.

The processor platform 2800 of the instant example includes a processor 2812. For example, the processor 2812 can be implemented by one or more microprocessors or controllers from any desired family or manufacturer. The processor 2812 includes a local memory 2813 (e.g., a cache) and is in communication with a main memory including a volatile memory 2814 and a non-volatile memory 2816 via a bus 2818. The volatile memory 2814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2816 may be implemented by flash memory and/or any other desired type of memory device. Access to the main memory 2814, 2816 is controlled by a memory controller.

The processor platform 2800 also includes an interface circuit 2820. The interface circuit 2820 may be implemented by any type of interface standard, such as an Ethernet interface, a universal serial bus (USB), and/or a PCI express interface.

One or more input devices 2822 are connected to the interface circuit 2820. The input device(s) 2822 permit a user to enter data and commands into the processor 2812. The input device(s) can be implemented by, for example, a keyboard, a mouse, a touchscreen, a track-pad, a trackball, isopoint and/or a voice recognition system.

One or more output devices 2824 are also connected to the interface circuit 2820. The output devices 2824 can be implemented, for example, by display devices (e.g., a liquid crystal display, a cathode ray tube display (CRT), etc.). The interface circuit 2820, thus, typically includes a graphics driver card.

The interface circuit 2820 also includes a communication device such as a modem or network interface card to facilitate exchange of data with external computers via a network 2826 (e.g., an Ethernet connection, a digital subscriber line (DSL), a telephone line, coaxial cable, a cellular telephone system, etc.).

The processor platform 2800 also includes one or more mass storage devices 2828 for storing software and data. Examples of such mass storage devices 2828 include floppy disk drives, hard drive disks, compact disk drives and digital versatile disk (DVD) drives. The mass storage device 2828 may implement a local storage device.

Coded instructions 2832 associated with flow diagrams and/or other figures described and disclosed herein may be stored in the local memory 2813, the mass storage device 2828, in the volatile memory 2814, in the non-volatile memory 2816, and/or on a removable storage medium such as a CD or DVD.

Various inventions have been described in sufficient detail with a certain degree of particularity. It is understood to those skilled in the art that the present disclosure of embodiments has been made by way of examples only and that numerous changes in the arrangement and combination of parts may be resorted without departing from the spirit and scope of the present disclosure as claimed. While the embodiments discussed herein may appear to include some limitations as to the presentation of the information units, in terms of the format and arrangement, the embodiments have applicability well beyond such embodiment, which can be appreciated by those skilled in the art. Accordingly, the scope of the present disclosure is defined by the appended claims rather than the forgoing description of embodiments.

The invention claimed is:

1. A method to surface varying degrees of patient data via a formlet-based user interface, the method comprising:
providing a high-level view of data for one or more patients, the high-level view having a first level of detail formed from a first set of one or more formlets built from detailed clinical models organizing content, the content providing parameterization of instructions telling the user interface how to operate in conjunction with the data;
generating, in response to a hover over a portion of the high-level view, a hover view providing a second level of detail of the data associated with the portion of the high-level view, the second level of detail formed from a second set of one or more formlets;
providing an inspector to access a third level of detail of the data, the third level of detail formed from a third set of one or more formlets; and
generating a fourth level of detail in response to a trigger within the inspector, the fourth level of detail formed from a fourth set of one or more formlets,
wherein each formlet in the first, second, and third sets specifies a display of content via the user interface according to the detailed clinical model associated with the content, and wherein each of the first, second, and third sets defines a form providing an application or view via the user interface based on the associated first, second, or third set of one or more formlets.

2. The method of claim 1, wherein the high-level view comprises a multi-patient view formed from a plurality of formlets.

3. The method of claim 1, wherein providing the inspector further comprises providing the inspector based on a selection of the hover view.

4. The method of claim 1, further comprising facilitating navigation of a variety of detailed information via one or more tabs provided in conjunction with the inspector.

5. The method of claim 1, further comprising enabling navigation between a multi-patient view and a single-patient view.

6. The method of claim 1, further comprising providing clinical analytics and decision support with respect to each of the first, second, third, and fourth levels of detail.

7. The method of claim 1, further comprising facilitating, via the hover view, context-based provision of information, wherein a plurality of hover views are available based on the portion of the high-level view.

8. A computer readable storage device or storage disk including computer program code to be executed by a processor, the computer program code, when executed, to implement a method to surface varying degrees of patient data via a formlet-based user interface, the method comprising:

providing a high-level view of data for one or more patients, the high-level view having a first level of detail formed from a first set of one or more formlets built from detailed clinical models organizing content, the content providing parameterization of instructions telling the user interface how to operation in conjunction with the data;

generating, in response to a hover over a portion of the high-level view, a hover view providing a second level of detail of the data associated with the portion of the high-level view, the second level of detail formed from a second set of one or more formlets;

providing an inspector to access a third level of detail of the data, the third level of detail formed from a third set of one or more formlets; and generating a fourth level of detail in response to a trigger within the inspector, the fourth level of detail formed from a fourth set of one or more formlets, wherein each formlet in the first, second, and third sets specifies a display of content via the user interface according to the detailed clinical model associated with the content, and wherein each of the first, second, and third sets defines a form providing an application or view via the user interface based on the associated first, second, or third set of one or more formlets.

9. The computer readable storage device or storage disk of claim 8, wherein the high-level view comprises a multi-patient view formed from a plurality of formlets.

10. The computer readable storage device or storage disk of claim 8, wherein providing the inspector further comprises providing the inspector based on a selection of the hover view.

11. The computer readable storage device or storage disk of claim 8, further comprising facilitating navigation of a variety of detailed information via one or more tabs provided in conjunction with the inspector.

12. The computer readable storage device or storage disk of claim 8, further comprising enabling navigation between a multi-patient view and a single-patient view.

13. The computer readable storage device or storage disk of claim 8, further comprising providing clinical analytics and decision support with respect to each of the first, second, third, and fourth levels of detail.

14. The computer readable storage device or storage disk of claim 8, further comprising facilitating, via the hover view, context-based provision of information, wherein a plurality of hover views are available based on the portion of the high-level view.

15. A system comprising:

a processor configured to implement:

an interface to provide a high-level view of data for one or more patients, the high-level view having a first level of detail formed from a first set of one or more formlets built from detailed clinical models organizing content, the content providing parameterization of instructions telling the user interface how to operation in conjunction with the data;

a hover view to a second level of detail of the data associated with the portion of the high-level view in response to a hover over a portion of the high-level view, the second level of detail formed from a second set of one or more formlets; and an inspector to provide access to a third level of detail of the data, the third level of detail formed from a third set of one or more formlets, wherein the inspector is to provide a fourth level of detail of the data in response to a trigger within the inspector, the fourth level of detail formed from a fourth set of one or more formlets, wherein each formlet in the first, second, and third sets specifies a display of content via the user interface according to the detailed clinical model associated with the content, and wherein each of the first, second, and third sets defines a form providing an application or view via the user interface based on the associated first, second, or third set of one or more formlets.

16. The system of claim 15, wherein the high-level view comprises a multi-patient view formed from a plurality of formlets.

17. The system of claim 15, wherein providing the inspector further comprises providing the inspector based on a selection of the hover view.

18. The system of claim 15, further comprising facilitating navigation of a variety of detailed information via one or more tabs provided in conjunction with the inspector.

19. The system of claim 15, further comprising enabling navigation between a multi-patient view and a single-patient view.

20. The system of claim 15, wherein the hover view is to facilitate, via the hover view, context-based provision of information, and wherein a plurality of hover views are available based on the portion of the high-level view.

* * * * *